United States Patent
Lopez-Avila et al.

(10) Patent No.: US 9,875,884 B2
(45) Date of Patent: Jan. 23, 2018

(54) AMBIENT DESORPTION, IONIZATION, AND EXCITATION FOR SPECTROMETRY

(71) Applicant: Agilent Technologies, Inc., Santa Clara, CA (US)

(72) Inventors: Viorica Lopez-Avila, Santa Clara, CA (US); Mark Denning, Santa Clara, CA (US); Mehrnoosh Vahidpour, Santa Clara, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 14/634,745

(22) Filed: Feb. 28, 2015

(65) Prior Publication Data

US 2016/0254133 A1    Sep. 1, 2016

(51) Int. Cl.

| | |
|---|---|
| *H01J 49/10* | (2006.01) |
| *H01J 49/04* | (2006.01) |
| *H01J 49/00* | (2006.01) |
| *H01J 49/16* | (2006.01) |
| *H05H 1/46* | (2006.01) |
| *G01N 21/71* | (2006.01) |
| *G01N 30/95* | (2006.01) |
| *H01J 27/16* | (2006.01) |

(52) U.S. Cl.
CPC .......... *H01J 49/102* (2013.01); *G01N 21/714* (2013.01); *H01J 49/0031* (2013.01); *H01J 49/0409* (2013.01); *H01J 49/049* (2013.01); *H01J 49/105* (2013.01); *H01J 49/161* (2013.01); *H05H 1/46* (2013.01); *G01N 30/95* (2013.01); *H01J 27/16* (2013.01)

(58) Field of Classification Search
CPC ...... H01J 49/10; H01J 49/105; H01J 49/0468; H01J 49/0472; H01J 49/049; H01J 49/107; H01J 49/102; H01J 49/0031; H01J 49/0409; H01J 49/161; H05H 1/46; G01N 21/73
See application file for complete search history.

(56) References Cited

U.S. PATENT DOCUMENTS

| | | | |
|---|---|---|---|
| 6,917,165 B2 * | 7/2005 | Hopwood | H05H 1/46 118/723 MP |
| 7,460,225 B2 * | 12/2008 | Karanassios | G01N 21/67 356/246 |

(Continued)

FOREIGN PATENT DOCUMENTS

WO    2014159588 A1    10/2014

OTHER PUBLICATIONS

Ratcliffe, L., et al., "Surface Analysis under Ambient Conditions Using Plasma-Assisted Desorption/Ionization Mass Spectrometry," Anal. Chem. 2007, 79, 6094-6101.*

(Continued)

*Primary Examiner* — Wyatt Stoffa

(57) ABSTRACT

An ion source includes a plasma generator for supplying plasma at an ionization region proximate to a sample surface. The plasma generator applies energy that may be utilized for desorbing analytes from the sample surface as well as for generating plasma by which analytes are excited or ionized. Desorption and ionization/excitation may be controlled as individual modes. The ion source may be interfaced with an ion-based or optical-based spectrometer. A sample support may be provided, which may be capable of performing analytical separation.

20 Claims, 13 Drawing Sheets

(56) References Cited

U.S. PATENT DOCUMENTS

| | | | | |
|---|---|---|---|---|
| 7,608,839 | B2* | 10/2009 | Coulombe | H01T 23/00 250/423 F |
| 7,700,039 | B2 | 4/2010 | Nagatsu | |
| 7,812,307 | B2* | 10/2010 | Dutton | H01J 37/32366 250/288 |
| 8,101,923 | B2 | 1/2012 | Orlando et al. | |
| 8,217,343 | B2* | 7/2012 | Cooley | H01J 49/107 250/288 |
| 8,237,135 | B2* | 8/2012 | Vanderberg | H01J 37/026 250/423 R |
| 8,736,174 | B2* | 5/2014 | Urdahl | H05H 1/2406 315/111.21 |
| 2005/0078309 | A1* | 4/2005 | Hammer | G01N 21/68 356/316 |
| 2005/0195393 | A1* | 9/2005 | Karanassios | G01N 21/67 356/316 |
| 2007/0170995 | A1* | 7/2007 | Dutton | H05H 1/46 331/107 R |
| 2011/0084203 | A1* | 4/2011 | Basile | C07K 1/12 250/282 |
| 2011/0108726 | A1* | 5/2011 | Hiraoka | H01J 49/165 250/282 |
| 2011/0168881 | A1* | 7/2011 | Sturgeon | H01J 49/145 250/282 |
| 2011/0180699 | A1* | 7/2011 | Cooley | H01J 49/162 250/282 |
| 2011/0309243 | A1* | 12/2011 | Whitehouse | H01J 49/0431 250/282 |
| 2013/0200257 | A1* | 8/2013 | Chapon | H01J 49/36 250/282 |
| 2013/0284915 | A1* | 10/2013 | Shimada | H01J 49/0404 250/282 |
| 2013/0299692 | A1* | 11/2013 | Shimada | H01J 49/0404 250/282 |
| 2013/0306856 | A1* | 11/2013 | Trimpin | H01J 49/16 250/282 |
| 2014/0312244 | A1* | 10/2014 | Shiea | H01J 49/107 250/423 R |
| 2015/0015140 | A1 | 1/2015 | Denning et al. | |
| 2015/0262804 | A1* | 9/2015 | Martinez Jarquin | H05H 1/2406 250/288 |
| 2016/0029472 | A1* | 1/2016 | Jevtic | H05H 1/46 250/288 |

OTHER PUBLICATIONS http://www.scbt.com/datasheet-204471.html, retrieved Jul. 19, 2016.*
Zhan, X., et al., "Microwave-Induced Plasma Desorption/Ionization Source for Ambient Mass Spectrometry," Anal. Chem., 2013, 85 (9), pp. 4512-4519.*
Houk, Robert S., et al. "Inductively coupled argon plasma as an ion source for mass spectrometric determination of trace elements." Analytical Chemistry 52.14 (1980): 2283-2289.*
Aleksandrov et al., "Mechanism of ultra-fast heating in a non-equilibrium weakly ionized air discharge plasma in high electric fields", J. Phys. D: Appl. Phys. 43 (2010) 255201 (19 pp).
Berkel et al., "Established and emerging atmospheric pressure surface sampling ionization techniques for mass spectrometry", J. Mass Spectrom 2005, 43: 1161-1180.
Chenea; "What can we learn from Ambient Ionization Techniques?" J. Am Soc Mass Spectrom 2009, 20, 1947-1963 Am Society for Mass Spectrometry.
Cheng et al., Building Blocks for the Development of an Interface for High-Throughput Thin Layer Chromatography/Ambient Mass Spectrometric Analysis: A Green Methodology, ACS Publications Anal. Chem 2012, 84, 5864-5858.
Chernetsova et al., "DART mass spectrometry and the applications in chemical analysis", Russian Chemical Reviews 80(3) 235-255 (2011).
Cooks et al., "Ambient Mass Spectrometry" Science 311, 1566, (2006).
Copty et al., "Low-power near-field microwave applicator for localized heating of soft matter", Applied Physics Letters 84, 5109 (2004).
Dole et al., "Molecular Beams of Macroions", The Journal of Chemical Physics 49, 2240 (1968).
Eshet et al., "Microwave Drilling of Bones", IEEE Transactions on Biomedical Engineering, vol. 53, No. 6, Jun. 2006.
Fuchsea, "Lipid analysis by thin-layer chromatography—A review of the current state", Journal of Chromatography A; 1218 (2011) 2754-2774.
Hrycak et al., "Spectroscopic investigations of microwave microplasmas—various gases/atmospheric pressure" Eur. Phys. J.D. 60, 609-619 (2010).
Iza and Hopwood, "Low-Power Microwave Plasma Source Based on a Microstrip Split-Ring Resonator", IEEE Transactions on Plasma Science vol. 31, No. 4, Aug. 2003.
Iza and Hopwood, Rotational, Vibrational, and Excitation Temperatures of a Microwave Frequency Microplasma, IEEE Transactions on Plasma Science vol. 32, No. 2, Apr. 2004.
Karas et al., "Influence of the Wavelength in High Irradiance Ultraviolet Laser Desorption Mass Spectrometry of Organic Molecules", Anal. Chem. 1985, 57, 2935-2939.
Kim et al., "Identification of Marker Compounds—Herbal Drugs on TLC with DART-MS" Arch Pharm Res. vol. 33, No. 9, 1355-1359, 2010.
Luftmann et al., "Automated Interface of hypenation of planar chromatography with mass spectrometry" Rapid Commun. Mass Spectrom, 2007, 21: 3772-3776.
NaNa et al., "Development of a Dielectric Barrier Discharge Ion Source of Ambient Mass Spectrometry" Am Society for Mass Spectrometry (2007) 1044-0305.
Ratcliffe et al., "Surface Analysis under Ambient Conditions Using Plasma-Assisted Desorption/Ionization Mass Spectrometry", Analytical Chemistry Jul. 12, 2007.
Whitson et al., "Direct Probe-Atmospheric Pressure Chemical Ionization Mass Spectrometry of Cross-Linked Copolymers and Copolymer Blends", Anal. Chem. 2008, 80, 7778-7785.
Cody et al., "Direct-Analysis-Real Time (DART tm) Mass Spectrometry" (8) JEOL News vol. 40 No. 1 (2005).
Ding et al.; "Plasma-based ambient mass spectrometry techniques: The current status and future prospective". Mass Spectrometry Reviews; vol. 34 No. 4; Dec. 13, 2013; pp. 449-473.
Partial European Search Report dated Aug. 12, 2016 from related European Application No. 16157116.1.
Salter et al.; "Importance of Sample Form and Surface Temperature for Analysis by Ambient Plasma Mass Spectrometry (PADI)". Analytical Chemistry; vol. 86 No. 18; Aug. 19, 2014; pp. 9264-9270.
Zhan et al.; "Microwave-induced Plasma Desorption/Ionization Source fir Ambient Mass Spectrometry". Analytical Chemistry; vol. 85 No. 9; Mar. 29, 2013; pp. 4512-4519.
Extended Search Report dated Jan. 9, 2017 from related European Application No. 16157116.1.
Huang, Yun-Qing et al., "Frontal elution paper chromatography for ambient ionization mass spectrometry: analyzing powder samples", Anal. Methods, 2013, vol. 5, pp. 4105-4111.
Jansen, G. W. et al., "Low-power microwave plasma source for chromatogapghy detection", Spectrochimica Acta, vol. 40B No. 1/2, pp. 307-316, 1985.

* cited by examiner

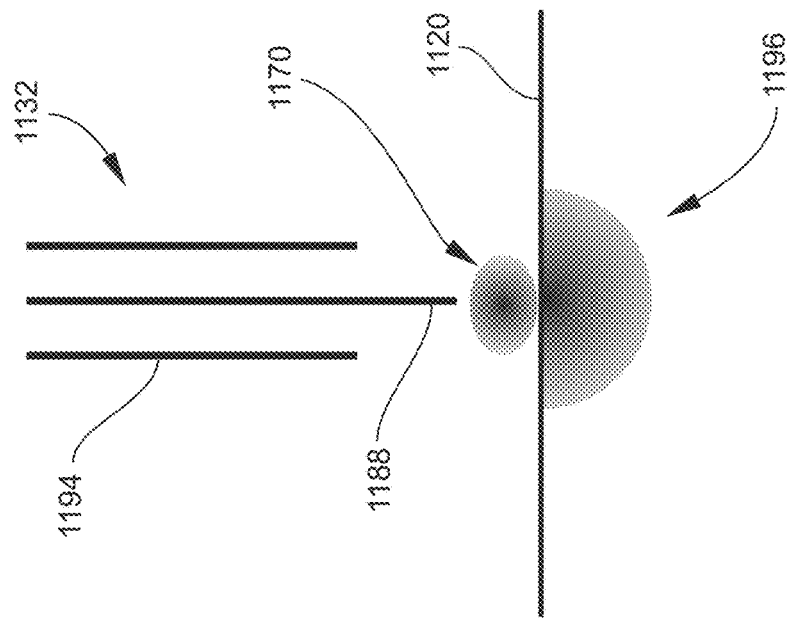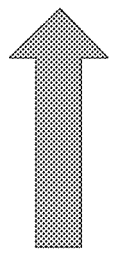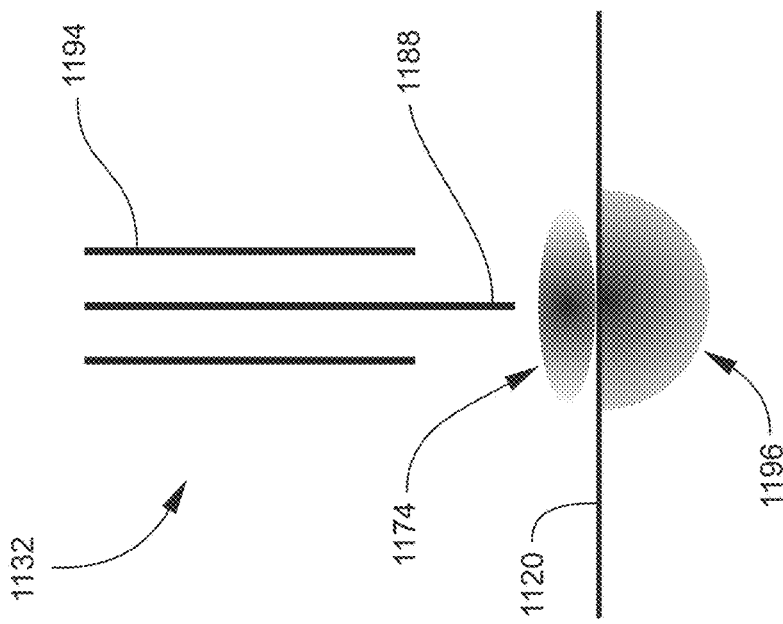
FIG. 11A
FIG. 11B

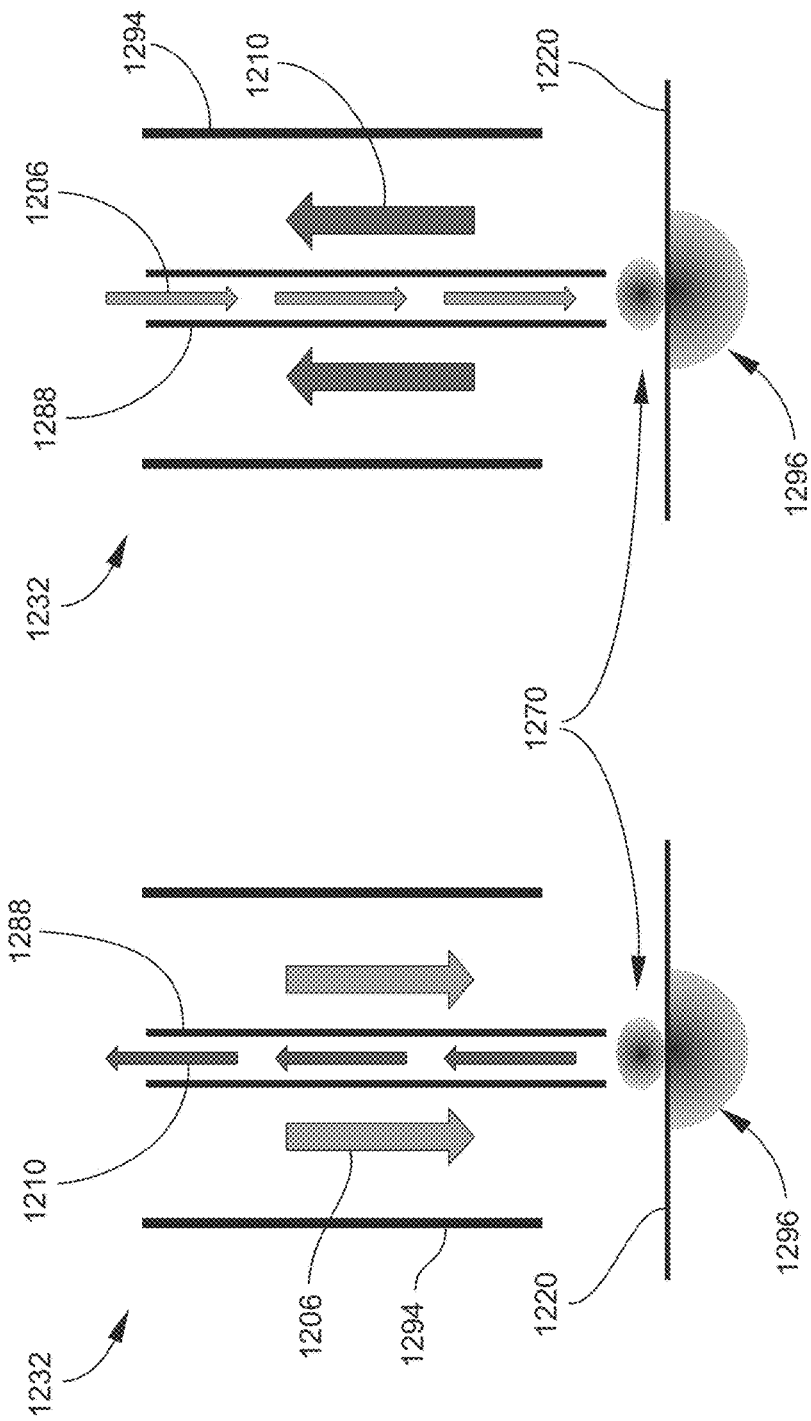

AMBIENT DESORPTION, IONIZATION, AND EXCITATION FOR SPECTROMETRY

TECHNICAL FIELD

The present invention relates generally to desorption of analytes from a sample material utilizing electromagnetic energy and/or plasma driven by electromagnetic energy, particularly microwave energy. The invention also relates to ionization and/or excitation of analytes utilizing plasma, and measurement of analyte ions or photons by a spectrometric/spectroscopic technique such as, for example, mass spectrometry (MS), ion mobility spectrometry (IMS), or optical emission spectroscopy (OES, also termed atomic emission spectrometry or AES). The invention further relates to devices, systems, and methods for implementing the foregoing.

BACKGROUND

Ambient ionization refers to a class of ionization techniques in which ions are formed in an ion source generally under ambient pressure conditions, and specifically outside of vacuum environment of a mass spectrometer (MS). Ambient ionization often, but not always, requires minimal or no sample preparation or analytical separation. Once analyte ions are formed they are transferred into the MS. Known methods for ambient sampling and ionization for mass spectrometry include direct analysis in real time (DART), electrospray ionization (ESI), and its many variants like desorption electrospray ionization (DESI), laser ablation ESI (LAESI), and matrix-assisted laser desorption and ionization (MALDI).

The DART technique typically entails generating a glow discharge plasma and flowing the plasma into contact with a sample whereby the plasma (primarily the metastable species) interacts with the sample. Depending on the feed gas used and the nature of the compounds under investigation, the DART technique can involve a highly complex set of ionization and fragmentation mechanisms. Penning ionization, impact ionization, and numerous chemical interactions occur between species that originate both in the discharge region as well as from the ambient air and the sample itself. In the absence of chromatographic separation, these reactions can result in highly complex and difficult-to-interpret mass spectra. Sample desorption in DART is convolved with plasma excitation and ionization. The DART technique therefore does not represent a practical method of analysis of unknown compounds. The DART technique typically requires substantial flow rates of discharge gas, typically in the range of 1 SLM (standard liter per minute) of helium. This level of gas consumption may not be economical for various applications, and would typically require large gas cylinders for frequent or continuous operation.

ESI techniques require the use of a solvent and a high-voltage needle. In ESI when implemented as an ambient ionization technique, particularly DESI, an electrically charged spray (electrospray) is produced when a high voltage is applied to a solvent, and the electrospray solvent droplets are attracted to a sample surface. Analytes from the sample are originally desorbed and then ionized by the charged aerosol. In laser-based ESI techniques, a pulsed laser incident on the sample surface ablates analytes from the surface, creating a plume of analytes above the surface and these analytes then interact with electrospray charged droplets to form ions. The ions produced by ESI-type techniques are introduced into an MS system via a vacuum interface.

MALDI requires the preparation of a sample in a matrix that acts as a laser absorber that facilitates laser ablation of a sample. The ablated and ionized sample molecules are then introduced into an MS system via a vacuum interface. MALDI is not appropriate for low molecular weight compounds (less than approximately 300 amu) due to interference from matrix peaks in the mass spectrum. That is, the matrix compounds typically employed in MALDI have molecular weights also less than 300 amu. Additionally the laser hardware used for MALDI is costly.

There is an ongoing need for devices, systems, and methods for performing analyte desorption and ionization while ameliorating or avoiding disadvantages associated with known ambient ionization techniques such as those noted above. There is also a need for such devices, systems, and methods that enable independent control over the respective desorption and ionization actions occurring during a sample run. There is also a need for such devices, systems, and methods that require little or no sample preparation or pre-treatment, or the use of solvents, or the use of costly high-precision instruments such as electrospray devices and lasers. There is also a need for such devices, systems, and methods that are capable of utilizing plasma for desorption, ionization, or both desorption and ionization. There is also a need for such devices, systems, and methods that are capable of generating plasma from a variety of different gas species instead of being limited to one or two species. There is also a need for such devices, systems, and methods that may be readily interfaced not only with mass spectrometers, but also with other ion-based spectrometers such as ion mobility spectrometers and further with optical-based spectrometers such as optical emission spectrometers.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, an ion source includes a plasma generator configured for supplying plasma at an ionization region proximate to a sample surface, the plasma generator comprising a plasma generating component configured for switching between operating in a desorption mode and in an ionization mode, wherein: in the desorption mode, the plasma generating component applies energy effective for heating the sample without generating plasma; and in the ionization mode, the plasma generating component applies energy effective for generating plasma from the plasma precursor gas; and an interface configured for transferring analyte ions or photons produced in the plasma to a spectrometer.

According to one embodiment, an ion source includes: a planar sample support comprising a sample surface and configured for performing analytical separation on the sample surface; and a plasma generator configured for supplying plasma at an ionization region proximate to the sample surface, the plasma generator comprising a gas outlet for supplying a plasma precursor gas, and a plasma generating component configured for generating a localized microwave energy field.

According to one embodiment, a spectrometry system includes: an ion source according to any of the embodiments disclosed herein; and an analyzer.

According to another embodiment, a method for ionizing a sample includes: providing a sample; desorbing analytes from the sample by applying electromagnetic energy under conditions effective for heating the sample without actively generating plasma; and generating plasma above a surface of the sample by applying the electromagnetic energy under conditions effective for generating the plasma, wherein the plasma ionizes the desorbed analytes.

According to another embodiment, a method for ionizing a sample includes: performing analytical separation on an initial sample on a sample surface of a planar sample support to produce a plurality of samples on the sample surface; and applying a localized microwave energy field to generate plasma above the sample surface proximate to a selected one of the samples, wherein the plasma ionizes analytes of the selected sample.

According to another embodiment, a method for analyzing a sample includes: ionizing a sample according to any of the embodiments disclosed herein to form analyte ions or photons; and measuring an attribute of the analyte ions or photons.

According to another embodiment, a spectrometry system is configured for performing any of the methods disclosed herein.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 11A is a schematic view of an example of a plasma generating component operating in a desorption mode according to some embodiments.

FIG. 11B is a schematic view of the plasma generating component illustrated in FIG. 11A, operating in an ionization mode according to some embodiments.

FIG. 12A is a schematic view of a coaxial MW guide according to other embodiments in which a flow of gas is provided.

FIG. 12B is a schematic view of the coaxial MW guide illustrated in FIG. 12A, in which the gas flow is different.

FIGS. 14A and 14B are schematic views of an example of an ion source configured for adjusting or varying the position of a plasma generating component relative to a sample surface according to some embodiments, wherein FIGS. 14A and 14B illustrate two different positions of the plasma generating component.

DETAILED DESCRIPTION

Figure 1:
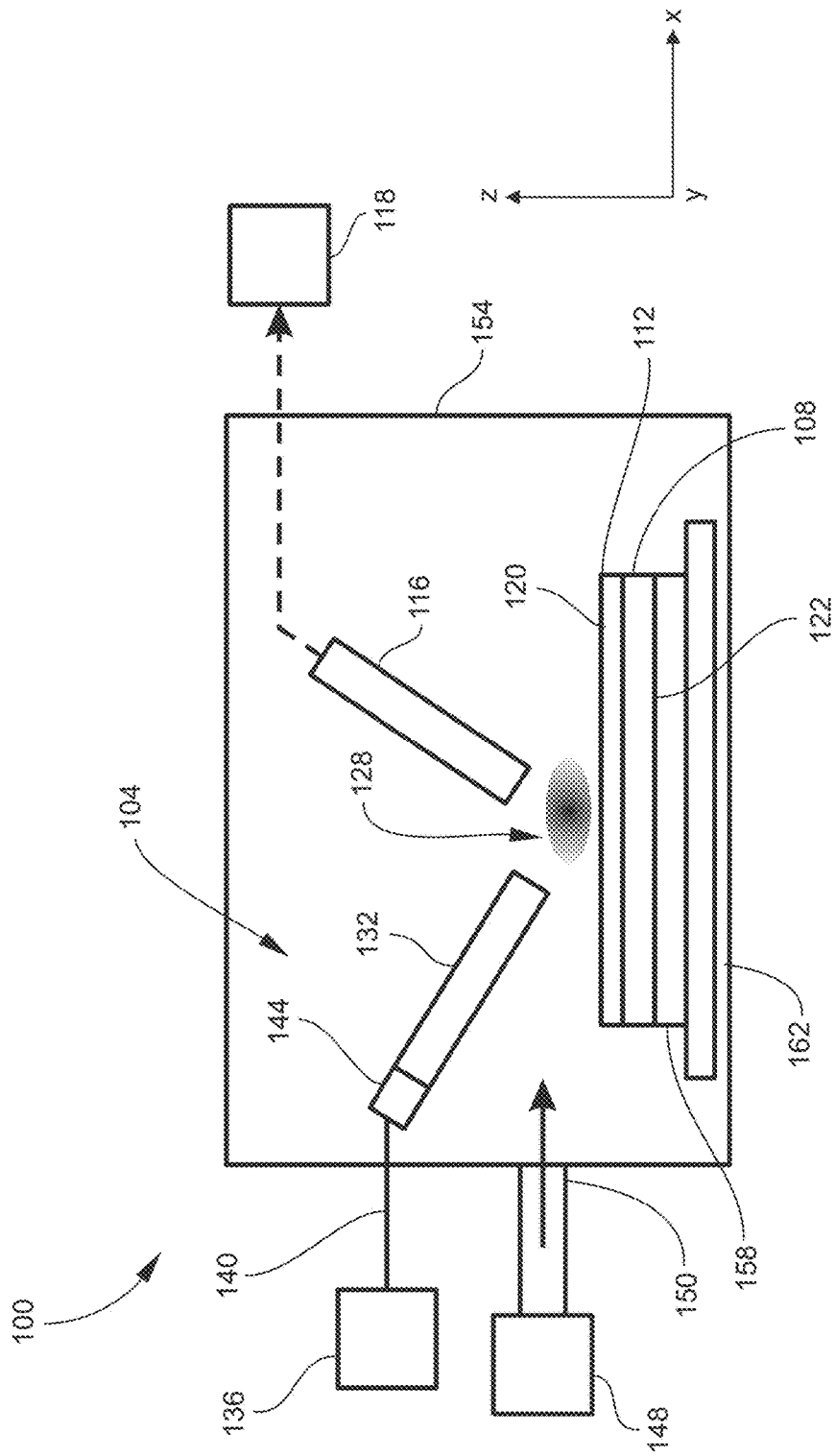
FIG. 1 is a schematic view of an example of a sample desorption and ionization device or system according to some embodiments, which may also be referred to as a plasma-based ionization device or plasma-based ion source.

Various embodiments described herein involve the generation of plasma. In the context of the present disclosure, a "plasma" is a mixture of particles (plasma species) that flows in a gas-like manner but is responsive to an electromagnetic field due to having a significant amount of charge carriers (plasma electrons and plasma ions). The plasma species include plasma electrons, plasma ions, metastable species (atoms or molecules that are electronically or vibronically excited but not ionized), and photons. For convenience, the term "plasma" encompasses neutral gas atoms and/or molecules that generally occupy the same space as the charged or excited plasma species, but have not been energized or ionized, or have returned to a neutral ground state (e.g., through de-excitation or recombination). That is, "plasma" may refer to a mixture of plasma species and neutral gas species. Plasma may also include certain free radicals, molecular fragments, and monomers. Certain additives such as dopants or reagents may also be included for various purposes, such as for chemically enhancing sample desorption or ionization. Such additives may be pre-mixed with the plasma-precursor gas (also referred to as a plasma-forming gas), or delivered locally to the plasma by a separate supply device.

In the context of the present disclosure, "plasma ions" are ions formed by generating and thereafter sustaining plasma from the plasma-precursor gas. Plasma ions thus are a species of the plasma itself. As such, "plasma ions" are distinguished from "analyte ions" (or "sample ions"), which are ions formed from sample material (sample atoms or molecules) through interaction between the sample material and one or more of the plasma species. Accordingly, analyte ions are the ions of interest in a given analytical procedure, as opposed to plasma ions.

Various embodiments described herein involve the use of plasma for ionizing sample material, i.e., producing analyte ions from the sample material. This process may be referred to as plasma-induced (or plasma-based) ionization. Depending on the embodiment, plasma-induced ionization may entail one or more different ionization mechanisms. Depending on the embodiment, two or more different ionization mechanisms may occur generally simultaneously, although one particular ionization mechanism may be the predominant ionization mechanism. Generally, plasma-induced ionization occurs when a plasma species interacts with a neutral analyte atom or molecule in a manner that causes the analyte atom or molecule to lose or gain an electron. One example is impact ionization, in which a collision between a high-energy plasma species and an analyte atom or molecule causes the analyte atom or molecule to lose an electron. A specific example is Penning ionization, in which a collision between a metastable species and an analyte atom or molecule causes the analyte atom or molecule to lose an electron. Another example is photo-ionization (PI), in which interaction between a plasma photon (typically of ultraviolet (UV) wavelength, particularly vacuum ultraviolet (VUV) wavelength) and a neutral analyte atom or molecule causes the analyte atom or molecule to lose or gain an electron. In many embodiments, the analyte ionization process induced by plasma is exclusively or predominantly soft ionization, i.e., achieves a high yield of molecular ions and higher mass diagnostic ions. However, in some embodiments the plasma conditions may be tailored to effect hard ionization when production of many fragment ions is desired.

In the broad aspects of the present disclosure, no specific limitation is placed on the composition of the plasma-precursor gas utilized to generate plasma. Examples include, but are not limited to, ambient air, helium (He), diatomic hydrogen ($H_2$), diatomic nitrogen ($N_2$), argon (Ar), neon (Ne), other noble gases, and mixtures of the foregoing species. In many embodiments, the plasma generated is a chemically nonreactive plasma, such as may be generated by energizing (exciting) argon or another monoatomic inert gas. A nonreactive plasma can ionize other molecules or sputter materials but is not itself consumed in chemical reactions. In other embodiments, the plasma may include reactive species. In embodiments in which PI is to serve a dominant role, it may be desirable to select a plasma precursor gas other than air so that UV photons are not absorbed by oxygen species.

In many embodiments the plasma generated is non-thermal plasma, also known as non-equilibrium plasma or cold plasma, in which plasma electron temperature is much higher than the temperature of the plasma ions and neutral species. However, the broad aspects of the present disclosure also encompass thermal plasma, in which plasma electrons, plasma ions, and neutral species are in thermal equilibrium.

In some embodiments, plasma may be actively struck and sustained directly in the same region sample material to be ionized or excited is located. This region may be referred to as the sample ionization region, sample excitation region, or sample interaction region. In other embodiments, plasma may be actively struck and sustained in a region (plasma generation region) that is at a (typically small) distance from the sample ionization region. In such embodiments, the sample material may be ionized through interaction with an afterglow of the plasma, in which the predominant plasma species are metastables, or photons, or both metastables and photons, as opposed to plasma ions and plasma electrons. For convenience, unless otherwise specified, the term "plasma" encompasses electrically active (energized) plasma, afterglow plasma, and partially extinguished plasma.

FIG. 1 is a schematic view of an example of a sample desorption and ionization device or system according to some embodiments, which may also be referred to as a plasma-based ionization device or plasma-based ion source 100. For illustrative purposes, FIG. 1 provides a Cartesian coordinate (x-y-z) frame of reference. The plasma-based ion source 100 generally includes a plasma generator (or plasma source) 104 configured for generating plasma, and an interface 116 configured for conducting analyte ions or analyte photons (photons emitted by analyte atoms or ions) to an analytical instrument 118. The ion source 100 is configured for desorbing analytes from a sample 112 such that the analytes become entrained as a sample plume in the space above the surface of the sample 112. The ion source 100 is also configured for establishing a localized interaction region or ionization region 128 just above the sample surface in which the analytes interact with the plasma to produce analyte ions and photons. The ion source 100 may be realized through various embodiments, some examples of which are described below. Depending on the embodiment, plasma may be generated at the ionization region 128 or transported a short distance to the ionization region 128.

In some embodiments, the ion source 100 includes a sample support 108 configured for supporting a sample 112 containing analytes of interest. The sample support 108 may generally include a sample surface (or first surface) 120 at which the sample 112 is disposed, an opposing back surface (or second surface) 122, and a thickness between the sample surface 120 and the back surface 122. In other embodiments the sample 112 may be held, manually or with the assistance of a manipulating (e.g., gripping) tool, in an appropriate position relative to the plasma generator 104 and the interface 116 such that analytes may be desorbed from a selected region of the sample 112.

The plasma generator 104 may generally include a plasma generating component 132 and a power supply 136. The power supply 136 may supply electromagnetic power to the plasma generating component 132 through a suitable power line 140. Depending on the embodiment, the power line 140 may be interfaced with the plasma generating component 132 via an appropriate power connector 144. In some embodiments, the ion source 100 also includes a gas supply or source 148 for supplying a plasma precursor (or plasma-forming) gas, i.e., the working gas utilized to strike and maintain the plasma, to the ion source 100 via a gas outlet 150. Depending on the embodiment, the gas outlet 150 may be configured (positioned, oriented, etc.) to establish a flow of gas directly to the ionization region 128 (as illustrated), or directly to the plasma generator 104 in which case the gas outlet 150 may be considered as being a part of the plasma generator 104. In other embodiments in which plasma is generated from ambient air, the gas supply 148 and gas outlet 150 are not needed.

In some embodiments, the plasma generator 104 may further include an auxiliary plasma initiation mechanism to reduce the overall microwave power requirement by providing seed electrons for plasma initiation. For example, the auxiliary mechanism may include an electrode and associated power source configured to emit a spark or arc, a focused pulsed laser, a relatively low-power microstrip resonator that assists plasma ignition of plasma powered by a high-power coaxial or waveguide slit source, etc. The auxiliary mechanism may be particularly useful if air is the working gas. In other embodiments, the plasma generator 104 is operated so as to apply an electric field of high enough intensity to achieve breakdown without the assistance of such a mechanism.

In some embodiments, the ion source 100 may operate in a fully open ambient environment. In other embodiments, the ion source 100 may include an enclosure 154 enclosing the ionization region 128 and at least parts of the plasma generator 104, sample support 108, and interface 116. The enclosure 154 may be desirable for constraining fluid and particle flows. In embodiments for which sub-atmospheric pressure operation is contemplated, the enclosure 154 may be sealed (fluid-tight) and include a vacuum port (not shown) for maintaining internal pressure at a desired sub-atmospheric level. However, for many embodiments operation at atmospheric pressure is desirable as it facilitates generating localized plasma and thus provides a spatially precise sampling mechanism, as well as being a less expensive alternative to vacuum-level operation.

The plasma generating component 132 and the interface 116 have been arbitrarily located and oriented in FIG. 1. Either or both of these components may be located directly above the ionization region 128, or on a lateral side (in the x-y plane) of the ionization region 128. In some embodiments, the plasma generating component 132 and the interface 116 may be integrated together, as described further below. In some embodiments, the plasma generating component 132 or a part thereof may be positioned below the sample support 108, i.e., on the side opposite to the sample 112, as also described further below.

The configuration of the plasma generator 104 depends at least in part on the type of electromagnetic excitation field utilized to strike and maintain the plasma. Various embodiments of the present disclosure encompass generating a microwave (MW) excitation field. In any of these embodiments, the excitation field may be a static or continuous wave (CW) field or a pulsed field. The plasma generating component 132 generally may be any component suitable for receiving power from the power supply 136 and coupling the microwave energy into the region where the plasma is to be generated. Depending on the embodiment, the plasma generating region may be co-located with the ionization region 128 or located a small distance away from the ionization region 128 as noted above. In the present context, "microwave" energy may generally refer to electromagnetic energy in the range of the radio frequency (RF) spectrum spanning Ultra High Frequency (UHF) to Extremely High Frequency (EHF), or 300 MHz to 300 GHz. Various embodiments disclosed herein may be effective at RF frequencies/wavelengths outside of the foregoing "microwave" range. Hence, the term "microwave" or MW may be considered interchangeably with the term "radio frequency" or RF.

Generally, the plasma generating component 132 may be a transmission line, resonant structure or cavity, waveguide, etc., which is configured to direct MW power to the plasma generating region (located at or a small distance away from the ionization region 128). The power line 140 may be a suitable transmission line such as a coaxial cable. The power connection 144 may be a standard design for RF/MW connections, such as a sub-miniature push-on (SMP) or sub-miniature type-A (SMA) coaxial connector. The plasma generating component 132 may include a field-focusing geometry or element effective for producing a highly localized, high-energy electromagnetic field (e.g., electrical field, or "E-field") useful for localized heating and/or plasma generation. Examples include, but are not limited to, a coaxial structure with an extended center conductor, a waveguide endplate with a slit, and a high-Q microstrip resonator with a small gap and/or electrode extension between microstrip ends. The plasma generating component 132 also typically includes an impedance matching device, which may be adjustable (i.e., a tuner). In some embodiments, the plasma generating component 132 may be positioned at the back surface 122 opposite to the sample side of the sample support 108, and the MW power is capacitively coupled to the sample side. This configuration may be desirable for physically isolating the plasma generating component 132 from the sample material and reducing the need for cleaning the plasma generating component 132 to remove contaminants.

As noted above, some embodiments include a sample support 108. The sample support 108 may be a substrate or plate presenting a sample surface 120 suitable for supporting a sample 112 to be desorbed and ionized. The sample surface 120 may be an outer surface of the bulk material of the substrate, or may be a layer (coating or film) on the substrate. The sample surface 120 may be an adsorbent material. The sample surface 120 may be a solid, a gel, or a fibrous (woven or non-woven) mat. The sample surface 120 may be porous, such as in the case of a membrane, filter, or monolithic porous structure. As non-limiting examples, the sample surface 120 may be composed of a ceramic, polymer, glass, gel, or cellulosic material. In some embodiments, the sample support 108 is configured for carrying out a surface-based (planar- or plate-based) analytical separation technique directly on the sample surface 120 such as, for example, thin-layer chromatography (TLC), paper chromatography, gel electrophoresis, Western blot, other blotting techniques, and techniques related to or derived from any of the foregoing.

In some embodiments, the sample support 108 is specifically composed of a dielectric material for the purpose of dielectric heating and/or capacitively or inductively coupling microwave energy across its thickness. In other embodiments, the sample support 108 may not be a good microwave energy absorber and thus may not itself be sufficiently responsive to dielectric heating. As one example, the sample support 108 may a thin glass plate such as is often utilized for TLC. In such cases, a microwave-absorbent material 158 may be positioned on the back surface 122 of the sample support 108 in good thermal contact therewith. In addition, as noted above, the plasma generating component 132 may be positioned at the back side of the sample support 108, and in this specific case at the microwave-absorbent material 158. The plasma generating component 132 may be operated at a power sufficient for heating the microwave-absorbent material 158 but lower than the plasma initiation threshold. Subsequently, the power may be increased to create plasma in the ionization region 128 above the sample support 108 via capacitive or inductive coupling through the microwave-absorbent material 158 and the sample support 108. Additionally or alternatively, heating of the sample 112 may be enhanced by pre-treating the sample 112 to improve its microwave absorptivity. For example, a microwave-absorbent liquid (e.g., water, acetone, etc.) or metallic or magnetic particles may be added to the sample 112.

The sample 112 may be wet or dried on the sample surface 120, and unprepared or prepared (untreated or treated), as needed for a particular embodiment. Generally, the sample 112 may be a matrix of analytes and non-analyte (background) material. In some embodiments, the sample 112 may be prepared or treated for a purpose such as facilitating adsorption to or desorption from the sample support 108, suppressing interfering components, reacting the sample 112, altering a property of the sample 112 (such as microwave absorptivity, as noted above), etc. Thus, in some embodiments the matrix may further include a solvent, reagent, dopant, or other additive.

In FIG. 1, the sample 112 is schematically depicted as a layer or film on the sample surface 120. However, this is not a limiting feature of the sample 112. More generally, the sample 112 may be a continuous mass spanning all or part of the sample surface 120, or may be a plurality of discrete samples 112 (e.g., spots, blots) distributed over all or part of the sample surface 120. The samples 112 may be arranged in a one-dimensional or two-dimensional array. The array may be a regular or ordered pattern with generally uniform distances between adjacent samples along a given direction, or may be an irregular or random pattern. An array of samples 112 may be created with the use of an appropriate dispensing device. In other embodiments, an array of samples 112 may be the result of an analytical separation technique (e.g., TLC, gel electrophoresis) in which different fractions of the sample material migrate along one or two dimensions on the sample surface 120. Thus, in the case of multiple samples 112 on the sample surface 120, the spatially separated samples 112 may have a generally uniform composition or alternatively may have different compositions (respective concentrations of different analytes), depending on the embodiment and on whether the original sample(s) were subjected to an analytical separation technique.

In some embodiments, the sample support 108 may be movable in one, two, or three directions. For example, the sample support 108 may be movable in one or both directions of the (x-y) plane occupied by the sample surface 120. In another example, the sample support 108 alternatively or additionally may be movable in the (z) direction perpendicular to the sample surface 120. The sample support 108 may be movable manually or in an automated manner. For example, the sample support 108 may be mechanically referenced to a one-, two-, or three-axis stage 162 or manipulated by a robotic end effector or gripper (not shown), as appreciated by persons skilled in the art. The sample support 108 may be moved to properly locate the ionization region 128 above the sample 112, i.e., to properly locate the sample 112 relative to the plasma or the plasma generating component 132, thereby ensuring interaction between the plasma and the sample 112. In some embodiments, the sample support 108 may be moved to adjust (vary) the distance between the plasma or the plasma generating component 132 and the sample 112. In some embodiments involving multiple samples 112, the sample support 108 may be moved to select which sample 112 of the array is to interact with the plasma.

In other embodiments, a sample support 108 is not employed. Instead the sample 112 may be supported manually or with a tool as noted above. As non-limiting examples, the sample 112 may be an object such as a food item, a piece of clothing or other material, an agglomeration of particles, etc. The sample 112 may be moved (translated and/or rotated, manually or with a tool) as desired to desorb analytes from different regions of the sample surface 120 or a subsurface thereof. Accordingly, in the context of the present disclosure, and depending on the nature of the sample 112 and whether or not a sample support 108 is employed, the term "sample surface" may refer to surface of a sample support 108 or to a layer thereon, the surface of a sample 112 adsorbed at the surface of a sample support 108, or the surface of a sample 112 unsupported by a sample support 108.

The configuration of the interface 116 depends on the type of analytical instrument 118 employed. For an ion-based analytical instrument (e.g., MS or IMS), the interface 116 may be a gas conductance-limiting aperture that leads into the first interior region (often a reduced-pressure stage) of the analytical instrument. Generally, the interface 116 in this case is configured to maximize ion transfer while minimizing neutral gas and liquid droplet transfer into the analytical instrument, and maintain a pressure differential between the ion source 100 and the analytical instrument 118. Examples of this type of interface include, but are not limited to, capillary-sized sampling conduits, sampling plates, skimmer plates, and the like as appreciated by persons skilled in the art. Analyte ions produced by the plasma are entrained in the gas flow above the sample 112 and carried generally toward the inlet into the interface 116. An electrical field may be utilized to attract the analyte ions and focus them into the interface 116, as appreciated by persons skilled in the art. For an optical-based analytical instrument such as optical emission spectroscopy (OES, also termed atomic emission spectrometry or AES), the interface 116 may be a light guide for collecting analyte photons and directing them into the analytical instrument. Generally, the interface 116 in this case configured to carry photons as efficiently as possible with minimal loss. The interface 116 of this type may be solid or hollow, such as an optical fiber or light pipe, and constructed of a material having a composition and index of refraction effective for reflecting photons internally (acting as a photon "mirror") to prevent their escaping the interface 116.

In various embodiments, the operation of the ion source 100 entails three actions: sample introduction, sample desorption, and sample ionization. First, the sample is introduced (or provided) to the ion source 100. As described above, in some embodiments sample introduction may involve positioning or holding the sample 112 in a proper position (i.e., at the ionization region 128) relative to the plasma generating component 132 and the interface 116. Such embodiments do not necessarily involve the use of a sample support 108. In other embodiments, sample introduction may involve the steps undertaken to adsorb the sample to an appropriate sample support 108 and position the sample support 108 relative to the plasma generating component 132, and may further involve analytical separation, as described above. Thereafter, sample material is removed (desorbed) from the sample surface 120 to facilitate ionizing or exciting the sample material through interaction with plasma at the ionization region 128 established just above the sample surface 120. Depending on the embodiment, sample desorption and sample ionization may occur essentially simultaneously, or in distinct sequential phases or modes (desorption followed by ionization), or the desorption and ionization phases or modes may be for the most part distinct but partially overlap in time. For example, simultaneous desorption and ionization may occur due to ionization of sample material taking place immediately upon liberation of that sample material from the sample surface 120, and/or due to ionization occurring directly at the sample surface 120, and/or due to desorption of sample material from the sample surface 120 continuing to occur while the plasma is actively ionizing previously desorbed sample material present in the ionization region 128. In another example, active plasma may not initially be present in the ionization region 128 at the start of the desorption mode. Instead, the plasma may be activated in (or transported to) the ionization region 128 a short time after desorption is carried out. In all such cases, desorption and ionization are both highly localized to the target sample 112 due to the field-focusing geometry of the plasma generating component 132.

In some embodiments, the plasma is utilized to effect desorption as well as ionization. In this case, one or a combination of mechanisms may contribute to desorption. One example is interaction between the energetic species of the plasma and the sample surface 120, which may be a physical interaction such as particle bombardment (e.g., sputtering). As one example, the plasma generator 104 may be configured to promote ion bombardment by imposing a spatial orientation on the electromagnetic excitation field that accelerates plasma ions to the sample surface 120. Another example of a desorption mechanism that may occur while the plasma is active is heating of the sample surface 120 (thermal desorption). Heating may entail dielectric heating by the excitation field utilized to sustain the plasma (particularly RF or MW heating), and/or radiative and convective heat transfer from the hot species of the plasma. Heating may additionally or alternatively entail dielectric heating of the sample support 108 followed by conductive heat transfer from the sample support 108 to the sample 112.

In other embodiments, the plasma generator 104 is configured for switching (one or more times) between operating in a desorption mode and in an ionization mode. Switching may entail switching the plasma between an OFF state in which the plasma has not yet been struck or has been extinguished, and an ON state in which the plasma is active through sufficient excitation by the electromagnetic field generated by the plasma generator 104. While the plasma is in the OFF state, desorption may occur by heating or both heating and particle impact, as described above. The thermal desorption mechanism may be more effective while the plasma is in the OFF state, because more electromagnetic power is available for absorption by the sample 112 instead of by the plasma (which may serve as an electromagnetic load that in effect shields the sample 112). In the present context, the OFF state of the plasma relates to an operating condition of the plasma generator 104 that is insufficient for striking and/or maintaining active plasma. Examples of switching the plasma between an OFF state and an ON state include, but are not limited to: switching application of the energy (electromagnetic field) between a low power or OFF state (insufficient to strike and/or maintain plasma) and a high power (or ON state), or between a non-resonant (e.g., low) drive frequency (insufficient to strike and/or maintain plasma) and a resonant (e.g., high) drive frequency; switching a flow of the plasma-precursor gas between an OFF (or insufficiently low flow) state and an ON (or high flow) state; and switching the plasma-precursor gas between a first composition having a high threshold for plasma formation and a second composition having a low threshold for plasma formation. As one example of the latter method the plasma generator 104 may be operated in ambient air, which has a high threshold power for plasma formation. A flow of a selected gas or gases (e.g., argon) may then be introduced, which would lower the threshold power and induce plasma formation provided the power is sufficient.

In other embodiments, switching between operating in a desorption mode and in an ionization mode may entail moving the position of the active plasma or the applied electromagnetic field relative to the sample 112 (and the intended ionization region 128). For example, the plasma generating component 132 may be moved away from the sample 112 such that the active plasma is too remote from the sample 112 to interact with it. Likewise, the sample 112 (or the sample support 108) may be moved away from the plasma generating component 132 as described above. As another example, the plasma generating component 132 may be moved toward the sample 112 such that the electromagnetic field (or at least the focus, or most intense portion, of the electromagnetic field) is below the sample 112. In this case, the electromagnetic field heats the sample 112 directly or indirectly by heating the sample support 108, but does not generate plasma in the ionization region 128 above the sample 112. In one specific example in which the plasma generating component 132 includes a coaxial waveguide with a center conductor, the center conductor may be moved to change the distance between a terminal end of the center conductor and the sample 112.

Figure 2A:
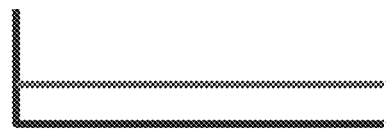
FIGS. 2A and 2B are plots of power (arbitrary units) applied by the device as a function of time (arbitrary units), illustrating an example of switching between a desorption mode (FIG. 2A) and an ionization mode (FIG. 2B).
Figure 2B:
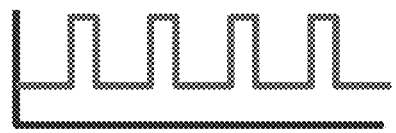
Figure 3:
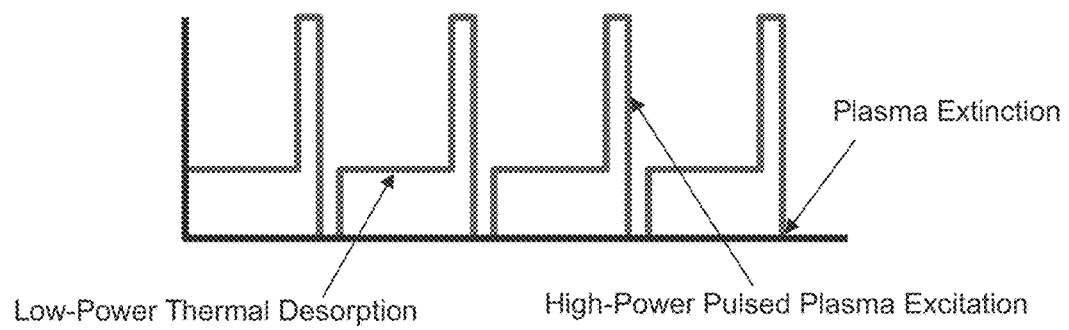
FIG. 3 is another plot of power as a function of time illustrating an example of implementing the desorption and ionization modes simultaneously.

FIGS. 2A and 2B are plots of power (arbitrary units) applied by the plasma generator 104 as a function of time (arbitrary units), illustrating an example of switching between a desorption mode (FIG. 2A) and an ionization mode (FIG. 2B). Specifically, FIG. 2A illustrates a low-power CW mode for carrying out thermal desorption. The energy applied by the electromagnetic field is effective for inducing localized heating at the sample surface 120, leading to desorption without necessarily inducing ionization of the analytes during this time. FIG. 2B illustrates a high-power pulsed mode for carrying out plasma excitation, whereby the plasma is struck and ionizes or excites the analytes. FIG. 3 is another plot of power as a function of time illustrating an example of implementing the desorption and ionization modes simultaneously. As shown, the plasma generator 104 is operated in two-level pulses separated by a short duration of time. At the beginning of each pulse, power is set to a low level to continuously heat the sample surface 120, and then is stepped up to a high level for plasma excitation. The power is then brought to zero for a brief period to extinguish the plasma. As shown, this process may be repeated one or more times.

In the desorption/ionization processes described above including those illustrated in FIGS. 2A, 2B, and 3, when the plasma is present the majority of the power will be deposited into the plasma and ambient gas, and when it is not present the power will be deposited into the sample surface 120. As also described above, gas heating and energetic plasma species may also contribute to sample desorption, supplementing direct heating by the electromagnetic field. The same plasma generator 104 may be run in a wide variety of modes (CW or pulsed plasma, thermal desorption only, thermal desorption/pulsed plasma, with/without plasma gas delivery, etc.) that may be chosen based on the application. Also in these embodiments, an auxiliary plasma initiation mechanism as described above may be utilized for each iteration of igniting the plasma.

In some embodiments, two or more plasma generators (or two plasma generating elements) may be employed in the ion source. One of more of the plasma generators may be dedicated for direct heating while one or more of the other plasma generators may be dedicated for plasma formation.

Implementation of the desorption mode distinct from the ionization mode may provide flexibility to the sample analysis and/or data acquisition. For example, the plasma generator 104 may be operated to apply the electromagnetic field in a controlled manner so as to heat the sample surface 120 slowly so that more volatile analytes are desorbed first, followed by less volatile analytes. This technique may be desirable for producing ions of the more volatile analytes first and thus simplifying the instantaneous spectra, or for eliminating the more volatile analytes and/or unwanted solvents from the spectra. The ion source 100 may include a suitable temperature probe (not shown) to monitor temperature, such as an infrared temperature sensor for monitoring the temperature of the sample surface 120, and provide feedback for carefully controlled heating.

In the case of an array of samples 112, the above-described implementations of sample desorption and ionization may be repeated for each sample 112 residing on the sample support 108 or a selected subgroup of these samples 112. This may be done by manually or mechanically indexing the sample support 108 so as to operatively align the selected sample 112 with the ionization region 128, as described above. Alternatively or additionally to sequential processing of multiple samples 112, the plasma generator 104 may include a plurality of plasma generating components 132 that may be operated concurrently to establish a plurality of concurrently active ionization regions 128, whereby multiple samples 112 may be processed simultaneously. In either the sequential or concurrent case, the analytical measurements taken on each sample 112 processed may be utilized to construct an analytical spectrum (mass spectrum, drift spectrum, atomic line spectrum, etc.) informative of the sample 112 under study. An example of utilizing multiple split-ring resonators to provide multiple plasma generation sites is described in U.S. Pat. No. 8,217,343, the entire content of which is incorporated by reference herein.

Likewise, the sample 112 if unsupported by a sample support 108 may be moved so as to extract analytes from different areas of its sample surface 120, as described above.

The plasma generator 104 may be operated in a heating mode for other purposes. For example, heating may be utilized to aid chemical reactions (e.g. derivatization) as part of the sample preparation and treatment, aid in drying the sample 112, or evaporate solvents.

Surfaces of the ion source 100 subject to contamination from the sample material and plasma constituents (e.g., plasma generating component 132, interface 116, other electrodes, etc.) may be cleaned between sample runs. In some embodiments, plasma may be utilized for cleaning. For this purpose, the plasma-precursor gas when utilized for cleaning may yield an energetic species found to be an effective cleaning agent, for example diatomic oxygen ($O_2$) or other oxygen-containing compound, diatomic hydrogen ($H_2$) or other hydrogen-containing compound, etc. The sample support 108 may be a relatively inexpensive item and thus may be readily disposable after a sample run, thereby eliminating the need for cleaning it.

Figure 4:
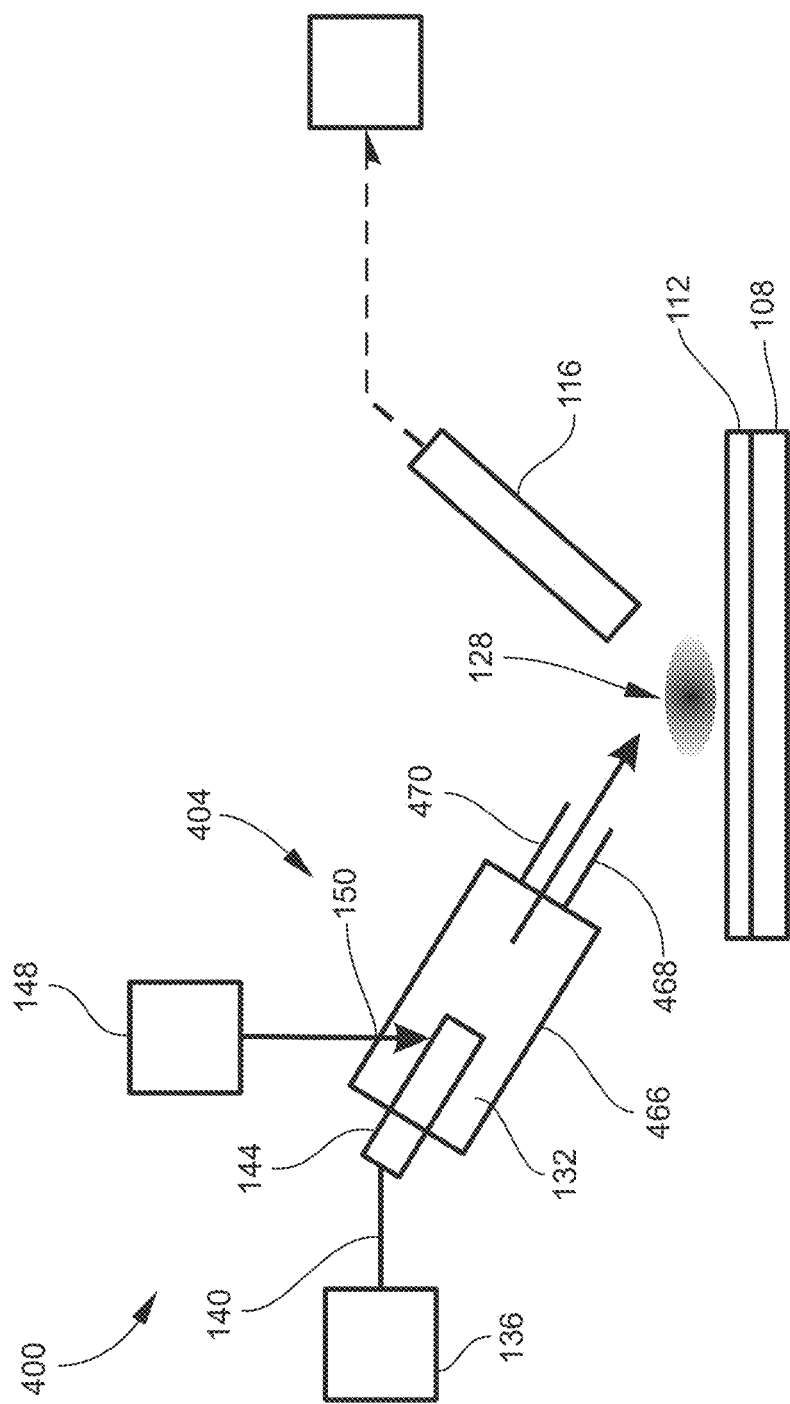
FIG. 4 is a schematic view of a sample desorption and ionization device or system (plasma-based ion source) according to other embodiments.

FIG. 4 is a schematic view of a sample desorption and ionization device or system (plasma-based ion source) 400 according to other embodiments. The plasma-based ion source 100 generally includes a plasma generator 404 configured for generating plasma, a sample support 108 configured for supporting a sample 112 containing analytes of interest, and an interface 116 configured for conducting analyte ions or analyte photons (photons emitted by analyte atoms or ions) to an analytical instrument 118 (FIG. 1). The plasma generator 404 may generally include a plasma generating component 132 and a power supply 136, and may further include a power line 140 and a power connector 144. As illustrated, the plasma generator 404 further includes a plasma containment structure or chamber 466. A gas supply 148 supplies a plasma precursor gas to the plasma chamber 466 via a gas outlet 150 communicating with the interior of the chamber 466. Alternatively, the gas outlet 150 may be a port for admitting ambient air into the chamber 466. All or part of the plasma generating component 132 may reside in the chamber 466 such that the plasma is struck and actively sustained inside the chamber 466. The chamber 466 includes a plasma outlet 468 (e.g., an orifice, nozzle, etc.) configured to direct the plasma to the ionization region 128. The flow of plasma through the plasma outlet 468 may be driven by the gas flow through the chamber 466. The plasma outlet 468 may be the open end of a conduit 470 extending from the main portion of the chamber 466.

The position and/or orientation of the plasma outlet 468, the conduit 470, or of the entire chamber 466, may be adjustable. In some embodiments, the chamber 466 and/or the conduit 470 may be configured to refine the composition of the plasma before the plasma reaches the ionization region 128. For example, the chamber 466 and/or the conduit 470 may allow for plasma electrons and plasma ions to recombine, or also for metastables to de-excite, such that the active plasma species in the ionization region 128 consist primarily of metastables and photons or primarily of photons. Further examples of utilizing plasma containment structures are described in above-referenced U.S. Pat. No. 8,217,343, and in U.S. Pat. No. 8,736,174, the entire content of which is incorporated by reference herein.

Figure 5:
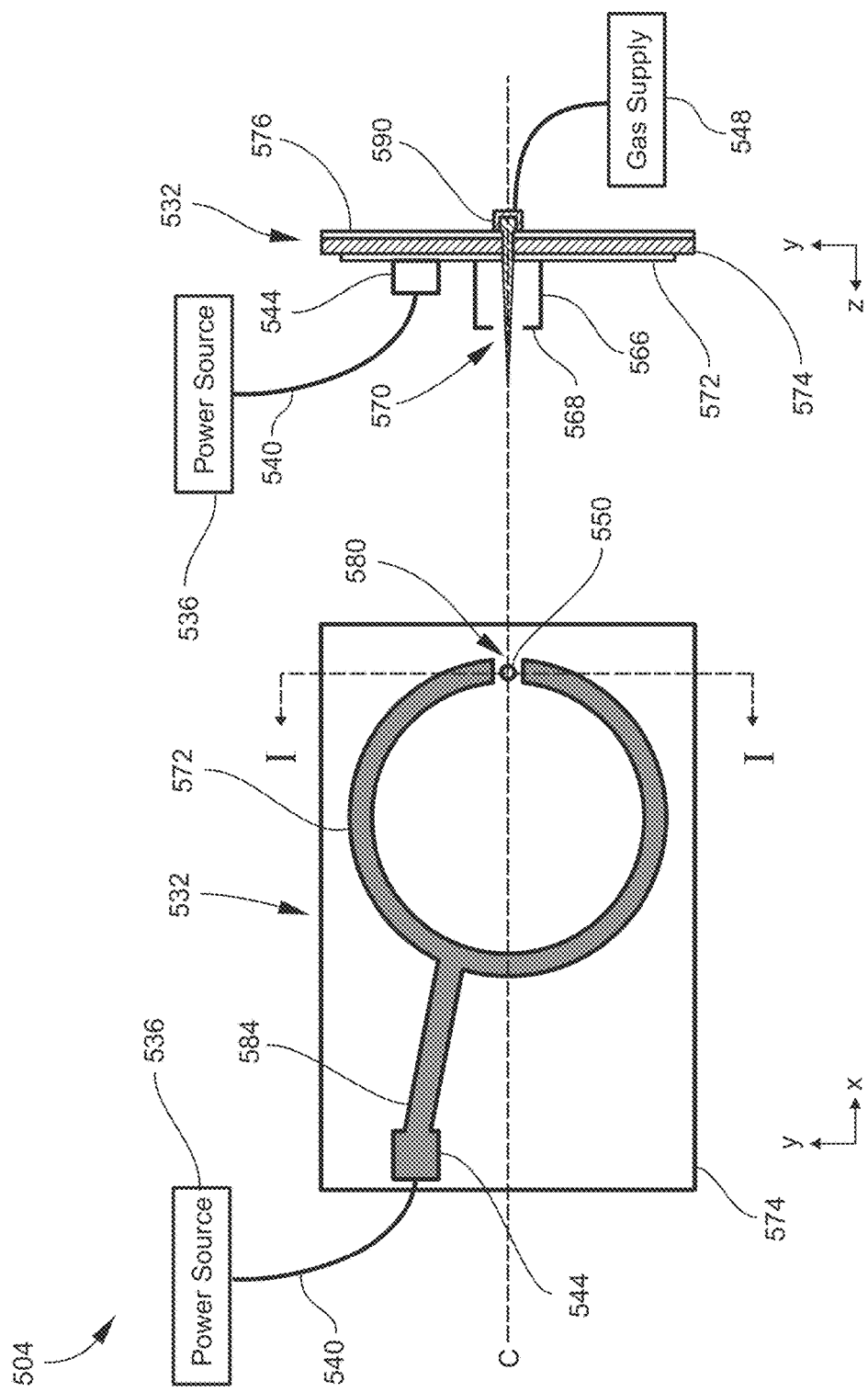
FIG. 5 is a plan view and side view of an example of a plasma generator according to another embodiment, which may be utilized in any of the ion sources described herein.

FIG. 5 is a plan view and side view of an example of a plasma generator 504 according to another embodiment, which may be utilized in any of the ion sources described herein. The plasma generator 504 includes a plasma generating component in the form of a split-ring resonator (SRR) 532. The SRR 532 may be constructed from a microstrip ring 572 disposed on a substrate or chip 574, with a ground plane 576 disposed on the opposite side of the substrate 572. The ring 572 has a closed-loop form except for a discharge gap 580 defined between two terminal edges of the microstrip. The ring 572 may be circular as illustrated, or may have another round shape or a polygonal shape. The SRR 532 may be fabricated or micro-fabricated by any suitable technique. Typically, the ring 572 is composed of a metal and the substrate 574 is composed of a dielectric material. A thin layer (<30 μm) of dielectric material may be applied to coat the electrode components to prevent erosion and sputtering by plasma. The plasma generator 504 may further include an MW power supply 536, a power line 540 and a power connector 544 to the ring 572. The power connector 544 may be coupled to a microstrip extension 584 leading to the ring 572 as illustrated, or directly to the ring 572. A gas supply 548 supplies a plasma precursor gas to a gas outlet 550 located in the discharge gap 580. The gas supply 548 may communicate with a gas feed connector 590 located on the back side of the substrate 574, from which gas flows through a bore in the thickness of the substrate 574 to the gas outlet 550. Alternatively, ambient air may be utilized without the need for a dedicated gas supply 548, as described above.

In operation, the plasma generator 504 generates a focused, high-intensity MW field at the discharge gap 580, and generates localized plasma (or "micro-plasma") at the discharge gap 580 when gas is supplied thereto. The components of the plasma generator 504 may be sized and shaped to optimize impedance matching before and after the plasma is generated. The frequency of the power may be adjusted as needed for impedance matching. An adjustable impedance matching device (not shown) may also be included in some embodiments. The plasma generator 504 may be positioned in any orientation on the sample side or opposite side of the sample support 108 to establish the ionization region 128 above the sample 112 (FIG. 1). In some embodiments, the plasma generator 504 further includes a plasma containment structure or chamber 566 enclosing a space in which the plasma is generated. The chamber 566 includes a plasma outlet 568 through which plasma 570 flows to the ionization region 128. An SRR-based plasma generator of the type just described and illustrated in FIG. 5 is further described in above-referenced U.S. Pat. No. 8,736,174.

Figure 6:
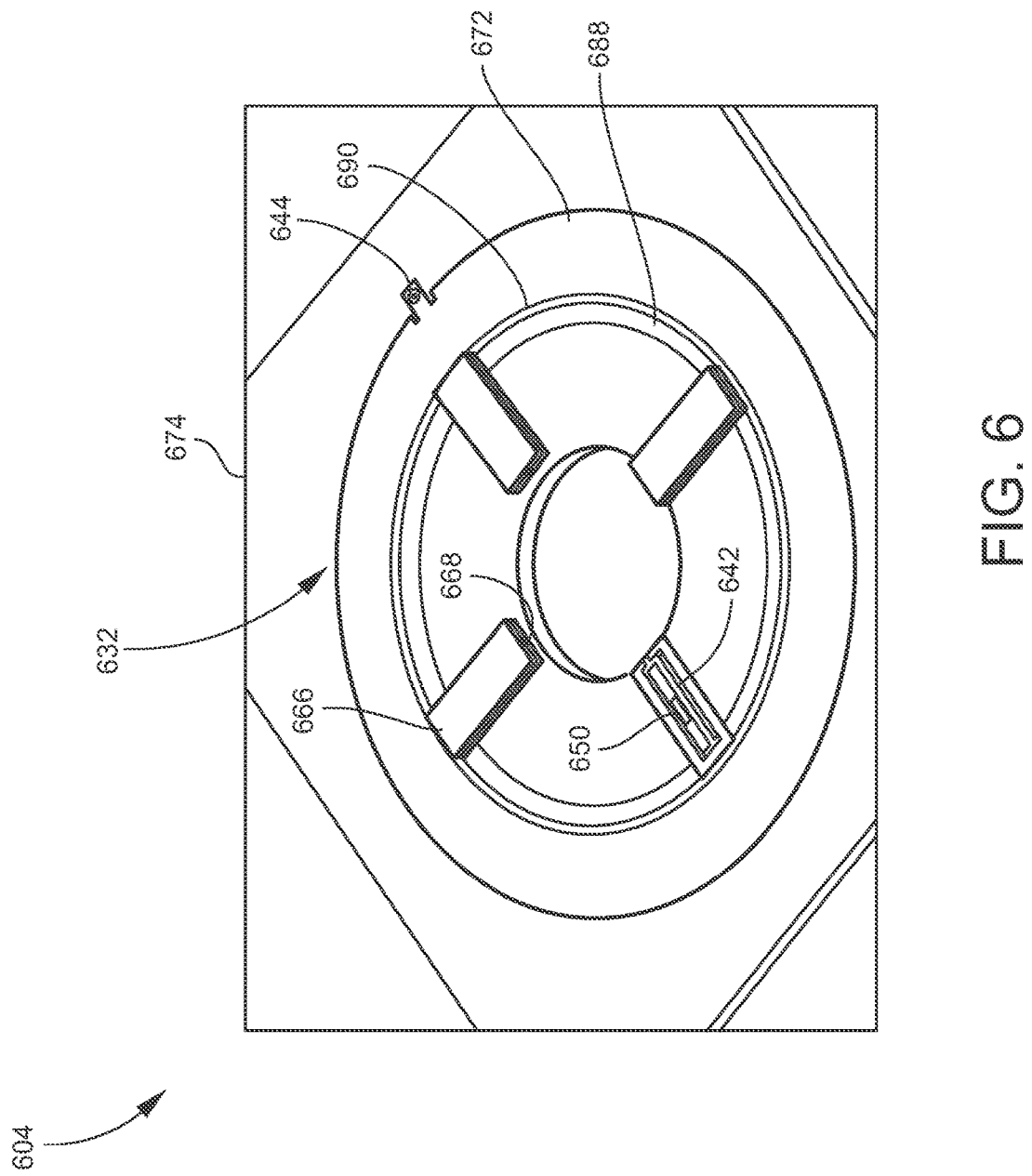
FIG. 6 is a perspective view of an example of a plasma generator according to another embodiment.

FIG. 6 is a perspective view of an example of a plasma generator 604 according to another embodiment. The plasma generator 604 includes a plasma generating component in the form of a coupled microstrip resonator (CMR) 632. The CMR 632 may be constructed from a first microstrip ring 672 and a second microstrip ring 688 disposed on a substrate or chip 674, with a ground plane (not shown) disposed on the opposite side of the substrate 674. The rings 672 and 688 are concentrically arranged and separated by a gap 690 whereby the rings 672 and 688 may be electromagnetically coupled. The rings 672 and 688 may be circular as illustrated, or may have another round shape or a polygonal shape. One of the rings 672 and 688 may be coupled to a MW power connector 644. One of the rings 672 and 688 may have terminal ends that are coupled to or transition to an electrode extension 692 configured for generating a focused, high-intensity field. The electrode extension 692 may be structured to define a gap in which a gas outlet 650 is located, or the gas outlet 650 may be located adjacent to the electrode extension 692. In operation, the plasma generator 604 generates a focused, high-intensity MW field at the electrode extension 692, and generates plasma at that located when plasma precursor gas is supplied by the gas outlet 650. Alternatively, ambient air may be utilized without the need for a dedicated gas supply, as described above. The plasma generator 604 may be positioned in any orientation on the sample side or opposite side of the sample support 108 to establish the ionization region 128 above the sample 112 (FIG. 1).

In some embodiments and as illustrated, the plasma generator 604 may include a plurality of electrode extensions 692 arranged around the ring 672 or 688 and corresponding gas outlets 650. By this configuration, the plasma generator 604 is capable of generating a plurality of localized electromagnetic fields and corresponding plasma at spatially distributed excitation sites, and thus a plurality of ionization regions 128 (FIG. 1) at these excitation sites. The excitation sites may be activated simultaneously, sequentially, or selectively by different means, such as controlling the gas flow to the respective sites, or structuring the electrode extensions 692 to have different resonant frequencies and controlling the frequency of the applied power, etc. This multi-site configuration may be useful for initiating desorption and/or ionization at different areas of the sample 112 (FIG. 1), or at different samples 112 that are arranged on the sample support 108.

In some embodiments and as illustrated, the electrode extension 692 and gas outlet 650 (or each electrode extension 692 and corresponding gas outlet 650 in the case of multiple excitation sites) are enclosed by a plasma containment structure or chamber 666, one of which is partially removed in FIG. 6 to show the electrode extension 692 and gas outlet 650. The chamber 666 includes a plasma outlet 668 through which plasma is emitted. The plasma outlet 668 positioned in any desired orientation to emit the plasma in any desired direction. In the illustrated embodiment, multiple plasma outlets 668 are oriented so as to all face radially inwardly toward a central area of the plasma generator 604, whereby multiple plasma plumes are directed toward this central area. By this configuration, multiple plasma plumes may be utilized to establish a single ionization region 128 (FIG. 1) at the central area. This configuration may be desirable for providing a high level of plasma photon emission while avoiding the saturation limit of emission associated with a given level of input power.

In other embodiments, the plasma generator 604 may include only one resonating ring 672 or 688. A CMR-based plasma generator of the type just described and illustrated in FIG. 6 is further described in U.S. Patent Application Pub. No. US 2015/0015140, the entire content of which is incorporated by reference herein.

Figure 7A:
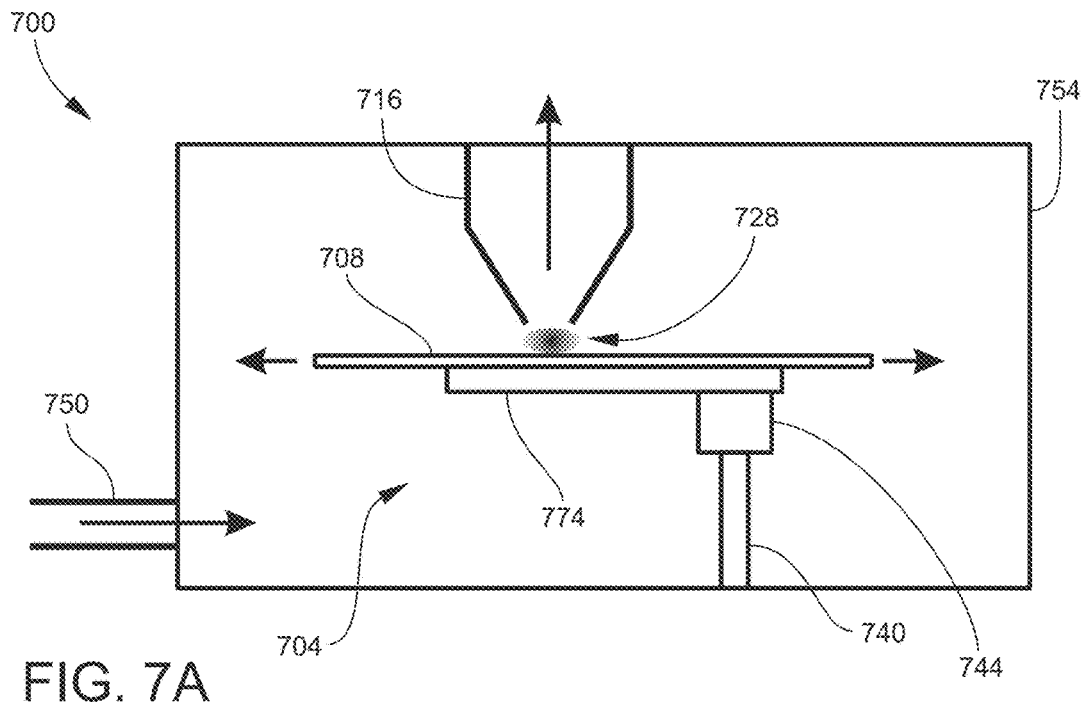
FIG. 7A is a schematic side view of an example of a plasma-based ion source according to other embodiments.
Figure 7B:
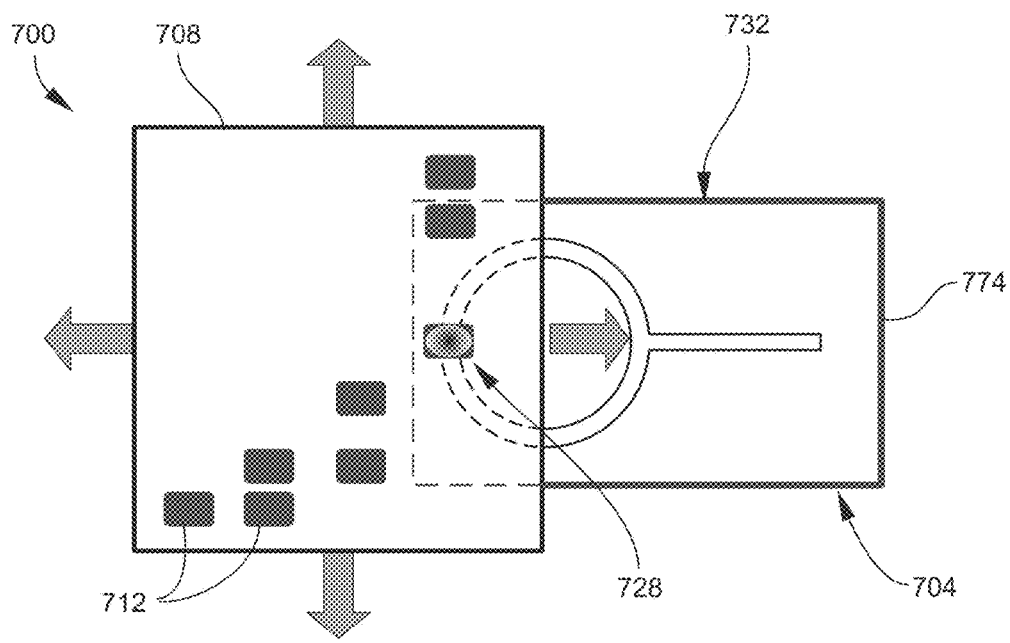
FIG. 7B is a schematic top plan view of the plasma-based ion source illustrated in FIG. 7A.

FIGS. 7A and 7B are respective schematic side and top plan views of an example of a plasma-based ion source 700 according to other embodiments. The ion source 700 generally includes a plasma generator 704 configured for generating plasma, a sample support 708 configured for supporting a sample 712 containing analytes of interest, and an interface 716 that in the illustrated example is configured for conducting analyte ions to a spectrometer (not shown). In this example, the plasma generator 704 includes a plasma generating component in the form of a microstrip resonator 732 fabricated on a substrate or chip 774, which may be configured as an SRR or CMR as described above and illustrated in FIGS. 6 and 7. MW power is supplied to the microstrip resonator 732 via a power line 740 (e.g., coaxial cable) and a power connector 744. The ion source 700 also includes a gas supply for supplying a plasma precursor gas to the ion source 700 via a gas outlet 750. In this example, the gas outlet 750 conducts gas into an enclosure 754 that encloses the sample support 108, the microstrip resonator 732, an ionization region 728 established by the microstrip resonator 732 above the sample surface, and a sampling orifice of the interface 716. Alternatively, ambient air may be utilized without the need for a dedicated gas supply, as described above. The plasma generator 704 may be operated in desorption and/or ionization modes as described above.

In the illustrated embodiment, the plasma generating component 732 is positioned below the sample support 708, i.e., on the back side opposite to the sample 712, such that the microstrip resonator 732 faces (and may be in contact with) the back side. Hence, the MW power is capacitively coupled to the sample side to generate plasma at the ionization region 728 above the sample surface. The ionization region 728 is located between the sample surface and the sampling orifice of the interface 716. In some embodiments, the interface 716 may be electrically biased to assist in extracting plasma-produced analyte ions from the ionization region 728 into the interface 716 as noted above.

Also in the illustrated embodiment, the sample material comprises a plurality of spatially separated samples 712 disposed on the sample surface of the sample support 708 for desorption and ionization by the plasma generator 704. The sample support 108 may be configured for carrying out a surface- or plate-based analytical separation technique directly on the sample surface, such as TLC or other methods noted above, in which case the respective samples 712 may contain different analytes as a result of the separation. Arrows in FIGS. 7A and 7B illustrate an embodiment in which the sample support 108 is movable relative to the plasma generating component 732, which as noted above enables a selected sample 712 to be operatively aligned with the focused excitation field generated by the plasma generating component 732 and thus with the ionization region 728.

Figure 8:
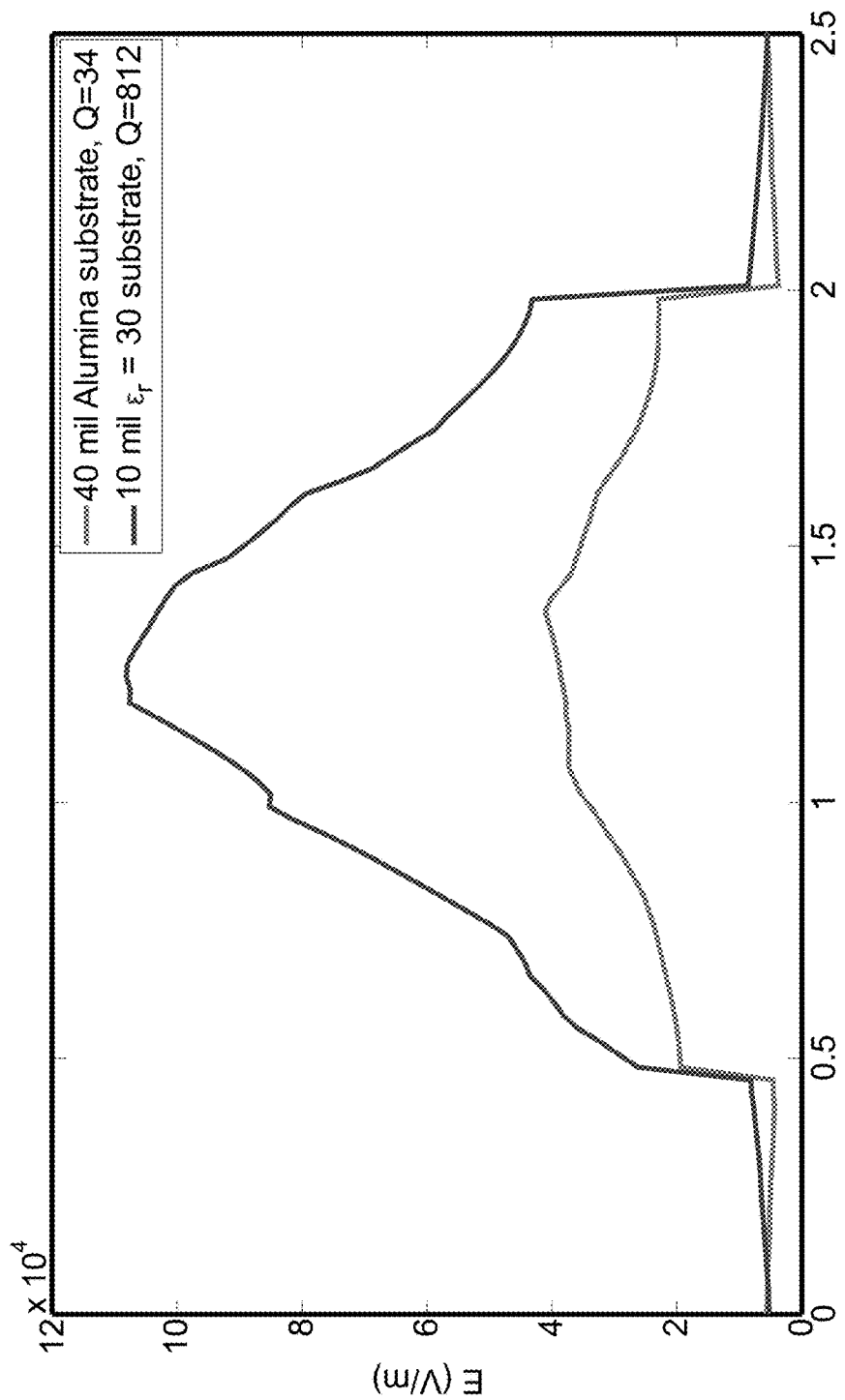
FIG. 8 compares the E-field intensity of two coupled microstrip resonator (CMR) chips with different substrate material and thickness.

Positioning a microstrip resonator such as the SRR and CMR described above on the back side of the sample support generates a gap between the microstrip electrodes and the plasma region. The farther the plasma region is from the electrodes, the weaker the E-field experienced by the plasma region will be. As a result, plasma initiation and sustaining will be more difficult. To enhance the E-field intensity at the presence of the sample surface, the Q-factor of the microstrip resonator should be enhanced. The Q-factor is defined as the ratio of energy stored to the energy dissipated in the resonator. Hence, a higher Q-factor is associated with lower dissipated energy and/or higher stored energy, and will enhance plasma initiation/sustaining. For a microstrip structure, thinner substrates and higher dielectric constants increase the Q-factor and as a result E-field distribution. FIG. 8 compares the E-field intensity of two CMR chips with different substrate material and thickness, specifically one material having a thickness of 40 mil (40 thousandths of an inch, or about 1016 μm) and composed of alumina and another material having a thickness of 10 mil (about 254 μm) and a relative permittivity of $\in_r=30$. The thinner and higher dielectric constant substrate has a higher Q and a higher E-field intensity as a result.

Waveguide-based cavities, or cavity resonators, may also be designed to generate a localized E-field in the RF spectrum and typically at MW frequencies. This may be done by providing a structural discontinuity (e.g., E- and H-plane diaphragms and irises) inside the waveguide which makes the fundamental mode of the waveguide intensified. For example, for rectangular waveguides a step discontinuity in the E-plane enhances the E-field intensity. With suitable impedance matching, the width of the waveguide can also be narrowed to reduce the total area and improve the spatial resolution of the sampling. To further improve the resolution, higher frequency cavities can be used (which have smaller cross-sections).

Figure 9:
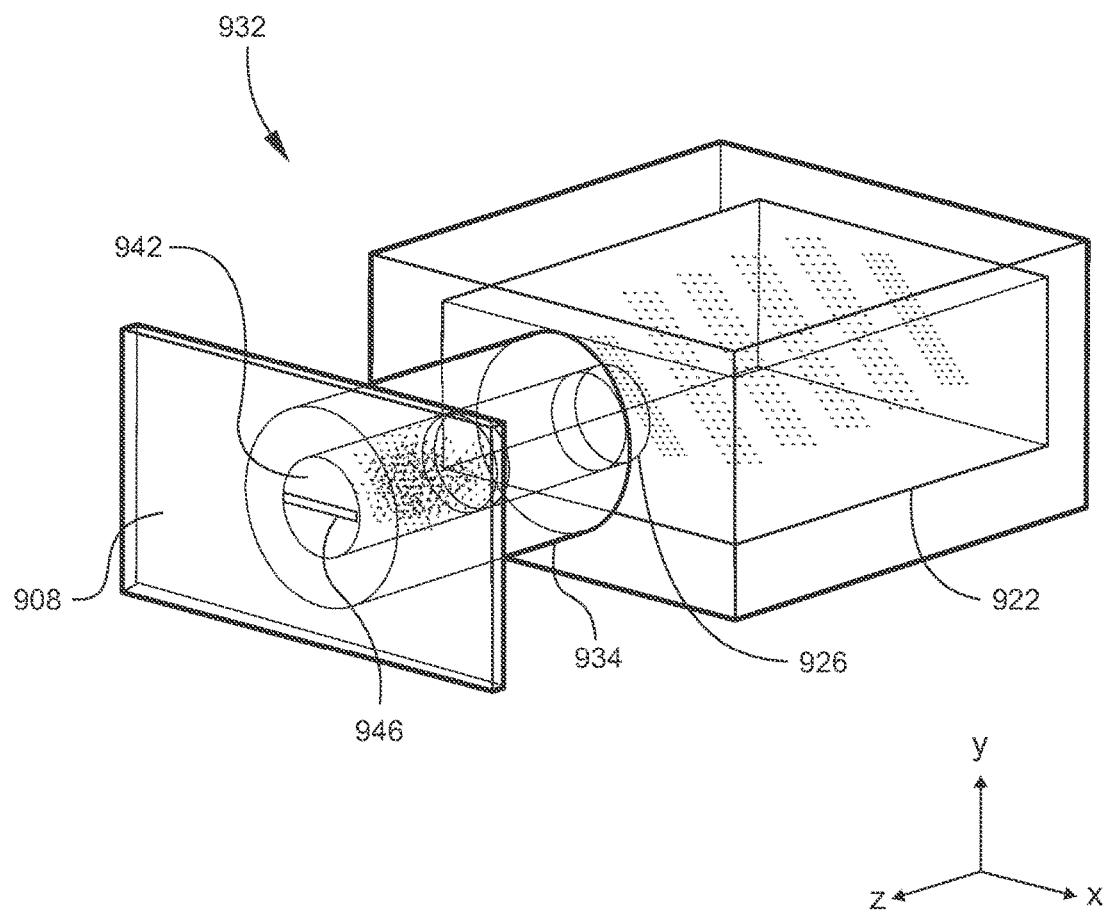
FIG. 9 is a schematic perspective view of an example of a plasma generating component in the form of a microwave (MW) cavity according to some embodiments.

FIG. 9 is a schematic perspective view of an example of a plasma generating component in the form of a microwave (MW) cavity 932. The MW cavity 932 includes a first waveguide portion 922 that transitions by way of a step discontinuity 926 to a second waveguide portion 934 of smaller cross-sectional area relative to the first waveguide portion 922. In the illustrated embodiment, the first waveguide portion 922 is rectangular and the second waveguide portion 934 is cylindrical. Alternatively, the first waveguide portion 922 may be cylindrical and the second waveguide portion 934 may be rectangular, or both may be rectangular or cylindrical. The second waveguide portion 934 terminates at an endplate 942 that has an aperture 946 at which a localized, high-intensity E-field is generated. In some embodiments, the aperture 946 may be shaped as a rectangular slit as illustrated. In one non-limiting example, the MW cavity 932 operates at 9 GHz and the size of the aperture 946 is 6 mm×400 μm (0.4 mm). As in one or more other embodiments described herein, the endplate 942 may be positioned at a small distance above the sample side of a sample support 908, or in contact with or very close to the back side of the sample support 908. See, e.g., Copty et al., "Low-power near-field microwave applicator for localized heating of soft matter," Appl. Phys. Lett., 84 (2004), p. 5109-5111.

Figure 10A:
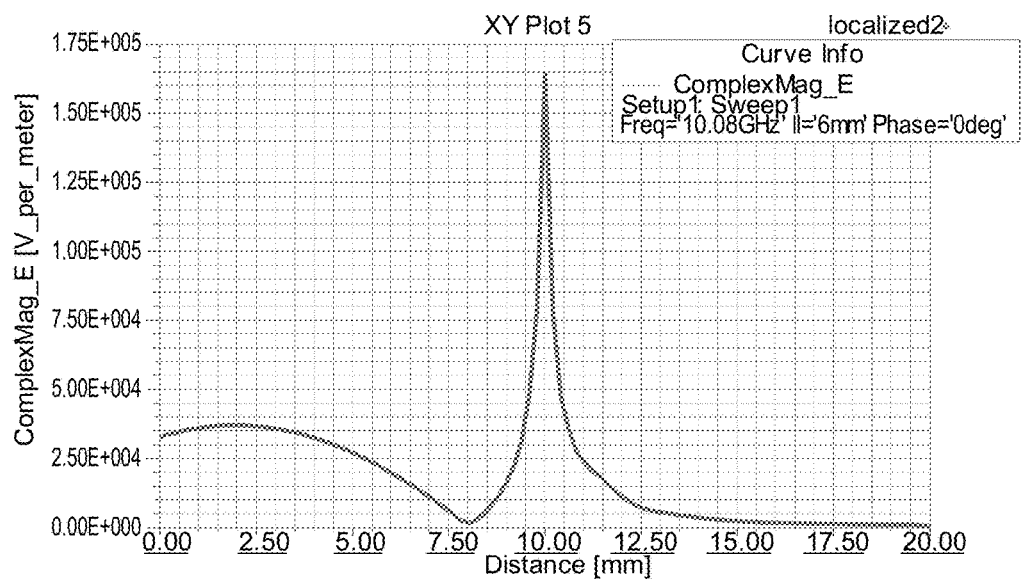
FIG. 10A is a plot of E-field intensity as a function of distance along the central (z) axis passing through an aperture of the MW cavity illustrated in FIG. 9.
Figure 10B:
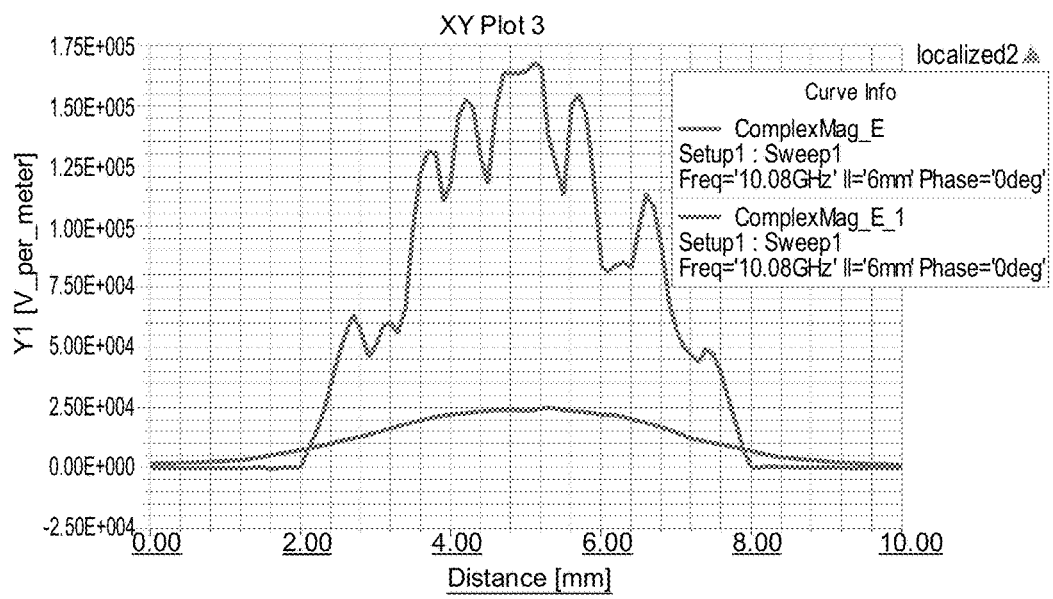
FIG. 10B is a plot of E-field intensity as a function of distance along the transverse (x) axis along which the aperture of the MW cavity illustrated in FIG. 9 is elongated.

FIG. 10A is a plot of E-field intensity as a function of distance along the central (z) axis passing through the aperture 946, and FIG. 10B is a plot of E-field intensity as a function of distance along the transverse (x) axis along which the aperture 946 is elongated. It is seen that the E-field intensity on the side of the sample support 908 opposite to the endplate 942, even though the intensity has dropped, is in the order of that of the above-described planar microstrip structures for the same input power. One advantage of using the waveguide cavity configuration is the feasibility of increasing the input power up to kW ranges. Therefore it is practical to increase the field intensity by numbers of orders of magnitude. If the very high field intensity on the front side of the plate raises concerns of damaging or melting the sample support 908, pulsed signals as described above may be used.

FIGS. 11A and 11B are schematic views of an example of a plasma generating component in the form of a coaxial microwave (MW) guide 1132 according to other embodiments. The coaxial MW guide 1132 generally includes a center conductor 1188 surrounded by an outer conductor 1194. The center conductor 1188 may extend to a distance beyond the terminal end of the outer conductor 1194. The dielectric medium between the center conductor 1188 and the outer conductor 1194 may be hollow or solid. The coaxial MW guide 1132 generates a focused, high-intensity MW field at the tip of the center conductor 1188. In the illustrated embodiment, the tip of the center conductor 1188 is positioned above a sample surface 1120. FIG. 11A illustrates operation of the coaxial MW guide 1132 in a thermal desorption mode, which may be carried out in accordance with FIG. 2A or 3 or other descriptions above. FIG. 11A illustrates heating 1196 of the sample surface 1120 and the bulk material below the sample surface 1120, resulting in a cloud of desorbed sample 1174 above the sample surface 1120. FIG. 11B illustrates operation of the coaxial MW guide 1132 in an ionization mode, which may be carried out in accordance with FIG. 2B or 3 or other descriptions above. FIG. 11B illustrates the generation of plasma 1170 between the tip of the center conductor 1188 and the sample surface 1120, i.e., in the ionization region where the desorbed sample 1174 is located, resulting in ionization of the desorbed sample 1174.

In some embodiments, switching between desorption and ionization modes may additionally or alternatively entail changing the relative position of the tip of the center conductor 1188 to the sample surface 1120 or vice versa (e.g., closer for MW heating, farther for plasma formation), as noted above. In some embodiments, the coaxial MW guide 1132 may be utilized as a "microwave drill" in which the center conductor 1188 causes localized heating and then is pressed into the sample material. This method may provide a modality for sampling a subsurface of the sample material. Once the surface has been penetrated, the plasma 1170 may be utilized to ionize or excite desorbed analytes that originated in the subsurface. See, e.g., Eshet et al., "Microwave Drilling of Bones," IEEE Trans. Biomed. Eng., Vol. 53, No. 6, p. 1174-1182, June 2006.

FIGS. 12A and 12B are schematic views of a coaxial MW guide 1232 according to other embodiments. The coaxial MW guide 1232 generally includes a center conductor 1288 surrounded by an outer conductor 1294. The coaxial MW guide 1232 operates as described above to cause heating 1296 of a sample surface 1220 and generate plasma 1270 between the tip of the central conductor 1288 and the sample surface 1220 for ionization/excitation of analytes. In the embodiments illustrated in FIGS. 12A and 12B, the space between the center conductor 1288 and the outer conductor 1294 is an open channel. Moreover, the center conductor 1288 is hollow.

In the embodiment of FIG. 12A, the coaxial MW guide 1232 is configured to establish a gas path through the channel between the center conductor 1288 and the outer conductor 1294 for delivering plasma precursor gas 1206 from a gas supply to the ionization region. Gas flow in this manner may also be useful for cooling the center conductor 1288 and/or other energized structures. The coaxial MW guide 1232 is also configured to establish a path through the hollow center conductor 1288 for delivering analyte ions or photons 1210 from the ionization region to an appropriate spectrometer. In an embodiment where photons are delivered, the center conductor 1288 may be configured to include a photon guide that maximizes photon transmission through the center conductor 1288, such as a layer of light-reflecting material as appreciated by persons skilled in the art. During photon uptake through the through the center conductor 1288, the coaxial MW guide 1232 may provide a flow of gas in either direction through the center conductor 1288 to protect optical surfaces in or downstream of the center conductor 1288 from being coated by desorbed and plasma-exposed products. Alternatively, the interior of the center conductor 1288 may be occupied by a solid light-transmitting material such as an optical fiber.

In the embodiment of FIG. 12B, the coaxial MW guide 1232 is configured to establish a gas path through the hollow center conductor 1288 for delivering plasma precursor gas 1206 to the ionization region, and a path through the channel between the center conductor 1288 and the outer conductor 1294 for delivering analyte ions or photons 1210 (more typically ions in this embodiment) from the ionization region to the spectrometer.

Figure 13:
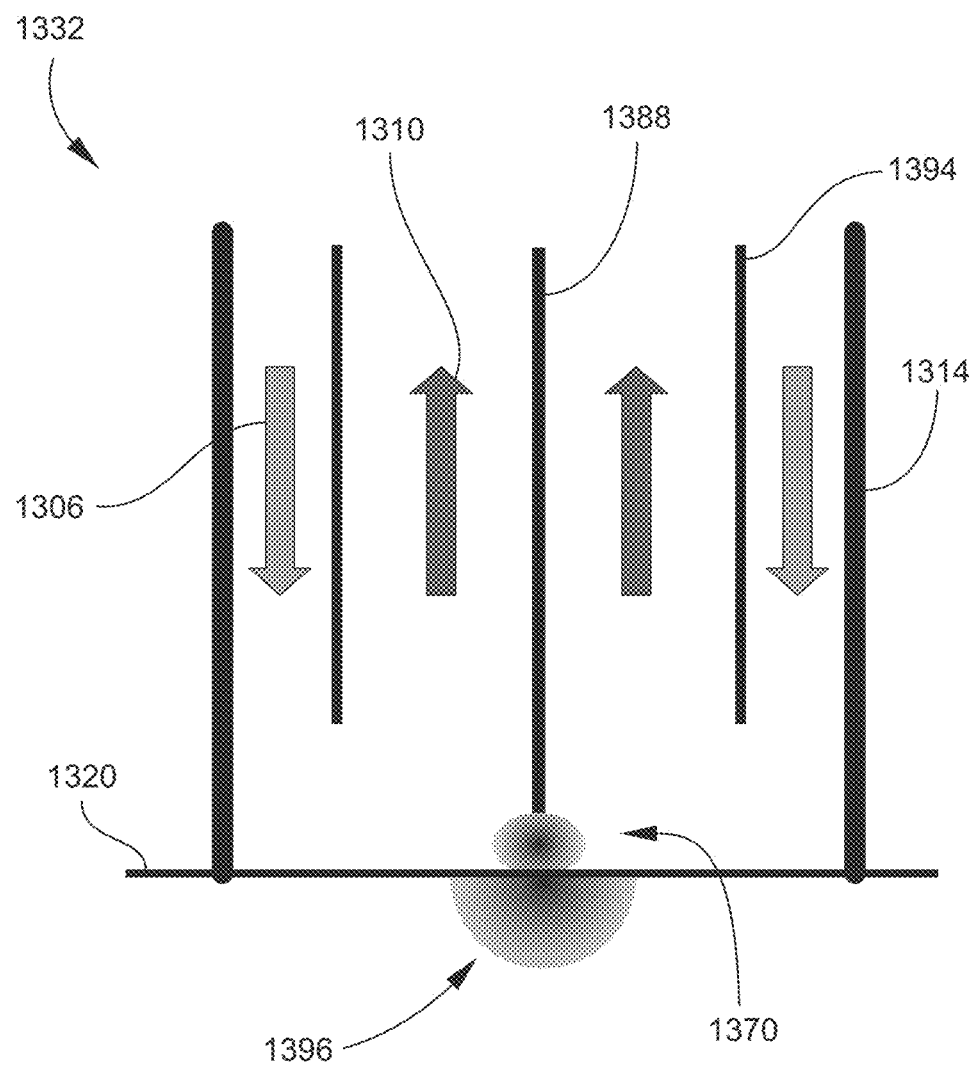
FIG. 13 is a schematic view of a coaxial MW guide according to other embodiments.

FIG. 13 is a schematic view of a coaxial MW guide 1332 according to other embodiments. The coaxial MW guide 1332 generally includes a center conductor 1388 surrounded by an outer conductor 1394. The coaxial MW guide 1332 operates as described above to cause heating 1396 of a sample surface 1320 and generate plasma 1370 between the tip of the central conductor 1388 and the sample surface 1320 for ionization/excitation of analytes. In the present embodiment, the space between the center conductor 1388 and the outer conductor 1394 is an open channel. In addition, another channel is formed between the outer conductor 1394 and a surrounding the outer conductor 1394. By this configuration, the coaxial MW guide 1332 is configured to establish a gas path through the channel between the sealing sleeve 1314 and the outer conductor 1394 for delivering plasma precursor gas 1306 to the ionization region, and a path through the channel between the between the outer conductor 1394 and the center conductor 1388 for delivering analyte ions or photons 1310 (more typically ions in this embodiment) from the ionization region to the spectrometer. The sealing sleeve 1314 may be desirable for providing a gas seal to ensure that plasma gas does not contain entrained air. For this purpose, the sealing sleeve 1314 may contact the sample surface 1320 but does not necessarily need to form fully fluid-tight or hermetic seal with the sample surface 1320. The sealing sleeve 1314 may also be used as a spatial reference point denoting the substrate location, and the relative distance of the microwave instrumentation to the surface can then be adjusted accordingly.

Figure 14A:
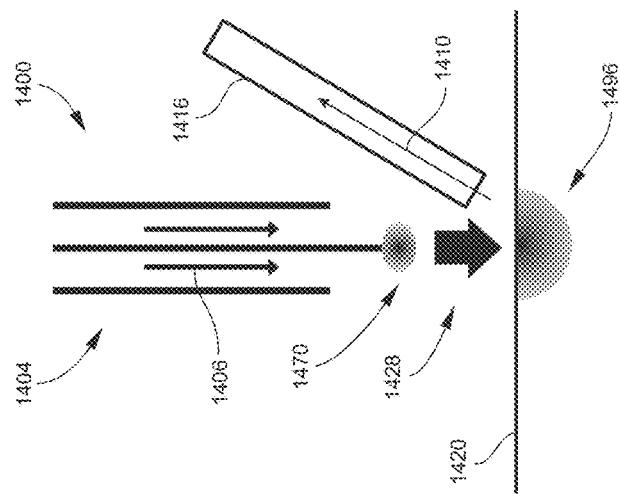
Figure 14B:
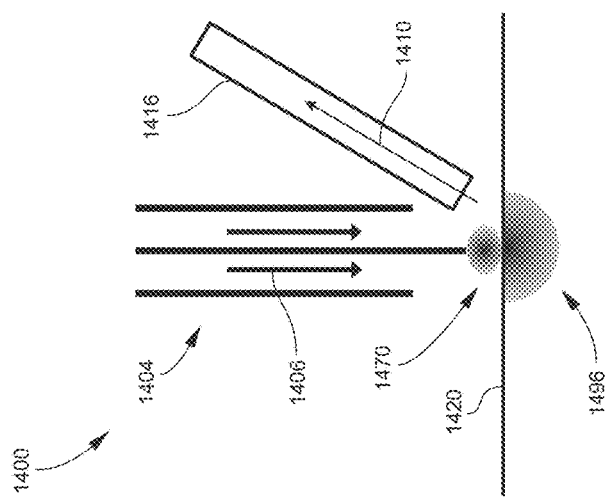

As described above, in some embodiments the delivery of excited plasma species may be tailored (or "refined") by positioning the region of plasma formation closer to or farther from the sample. If the region of plasma excitation is very close to the sample substrate and any desorbed sample present in the space above the substrate, the analytes will be exposed to a wide variety of excited species (high-energy electrons, plasma ions, metastables, UV photons). If, on the other hand, the plasma excitation region is farther from the sample, certain excited species may be eliminated from the plasma before it diffuses to the sample (e.g., three-body recombination of plasma electrons and ions at atmospheric pressure, UV photon absorption by ambient oxygen). FIGS. 14A and 14B illustrate an example of tailoring or refining a plasma. Specifically, FIGS. 14A and 14B are schematic views of an example of an ion source 1400 configured for adjusting or varying the position of a plasma excitation region 1470 relative to a sample surface 1420. The ion source 1400 includes a plasma generator 1404 and an interface 1415 positioned above the sample surface 1420. The plasma generator 1404 may have any configuration described herein that integrates the delivery of plasma precursor gas 1406 with the plasma generating element that applies the electromagnetic excitation field. In FIG. 14A, the plasma generating element is positioned close enough to the sample surface 1420 that the plasma excitation region 1470 is co-located with an ionization region 1428 at which the actively excited plasma interacts with the sample to produce analyte ions and photons from the sample surface 1420. In FIG. 14B, the plasma generating element has been moved farther away from the sample surface 1420 such that the plasma excitation region 1470 is located at some distance from the ionization region 1428. In this case, the sample interacts with a plasma afterglow comprising primarily metastables and/or photons. By varying the position of the plasma excitation region 1470 in this way, different ionization/fragmentation/excitation mechanisms may predominate, resulting in different analyte ions or photons 1410 being transferred to the spectrometer and consequently different mass spectra being produced. In both cases, the sample surface 1420 can be heated 1496.

The present disclosure also encompasses spectrometers (or spectrometry systems). Generally, a spectrometer or spectrometry system as disclosed herein includes a plasma-based ion source according to any of the embodiments disclosed herein, and an analytical instrument 118 (FIG. 1) interfaced to the ion source. As described above, the analytical instrument 118 may be an ion-based spectrometer (e.g., MS or IMS) or an optical-based spectrometer (e.g., OES or AES). For convenience, the term "spectrometer" or "spectrometry system" as used herein encompasses spectroscopy instruments and systems (the term "spectroscopy" often being associated with optical-based measurement/analysis) unless specified otherwise. Generally, the analytical instrument includes an analyzer for spectrally resolving analytes based on a discriminating attribute or property, a detector for measuring the analytes, and electronics for processing output signals from the detector as needed to produce user-interpretable spectral information. Depending on the embodiment, the spectral information may be utilized to identify molecular and/or elemental species of the sample under investigation, measure the abundance or concentration of the species in the sample, determine the molecular structures, conformations, isotopes, isomers, etc. of components of the sample, thereby enabling the sample to be qualitatively and quantitatively characterized.

In an MS system, the analyzer is a mass analyzer that separates the ions based on their differing mass-to-charge ratios (or m/z ratios, or more simply "masses"). Depending on design, the mass analyzer may separate ions by utilizing electric and/or magnetic fields, or time-of-flight tubes. The ion detector counts the ion masses, enabling the construction of a mass spectrum, i.e., a spectrum of mass peaks. The intensity of each peak is indicative of the abundance of each ion mass detected. Embodiments of the present disclosure also include tandem MS (MS-MS or MS$''$) systems, which employ more than one mass analyzer and a collision cell or other ion fragmentation device upstream of the final mass analyzer, as appreciated by persons skilled in the art. In an IMS system, the analyzer is a drift cell that separates ions based on their different collision cross-sections (CCSs). In a drift-time IMS system, ions are pulled through the drift cell by a DC voltage gradient in the presence of a drift gas. Ions of differing collision cross-sections have differing drift times through the gas environment. The ion detector counts the ions as they arrive at the ion detector, enabling the construction of a drift time spectrum. Drift time through an IM drift cell can be correlated to CCS and to a lesser extent ion mass. Alternatively, the IM drift cell may be configured to operate at or near atmospheric pressure, or may be configured as a field-asymmetric ion mobility spectrometry (FAIMS) cell as appreciated by persons skilled in the art. For convenience, the term "IM drift cell" encompasses FAIMS cells. Embodiments of the present disclosure also include hybrid IM-MS systems in which an IM drift cell is coupled with an MS to provide unique two-dimensional information about an analyte under investigation.

Certain embodiments of plasma-based ionization techniques disclosed herein may be utilized to break sample material down to atoms in preparation for elemental analysis, for example to measure the concentration of trace metals in the sample. The desorption mode may be utilized to convert the sample material on the sample support into an aerosol that readily interacts with plasma in the ionization region above the sample surface. Exposure to plasma breaks the sample molecules down to atoms, or alternatively partially breaks the sample molecules into molecular fragments. In the plasma, unbound electrons repeatedly collide with the sample atoms or ions. As a result of this process, the atoms or ions emit electromagnetic radiation (light, quantized as photons) at wavelengths characteristic of their elemental identities. Thus, in addition to ion-based spectrometers, a plasma-based ion source as disclosed herein may be coupled to an OES.

In an OES, this light is collected and focused by optics and directed to an analyzer, which may include, for example, a diffraction grating. The analyzer spectrally resolves the light into its component wavelengths, enabling the intensity of the light at each wavelength to be measured by an optical detector. The OES system then presents the data so acquired as a spectrum of atomic emission lines. The intensity of each line is indicative of the concentration (abundance) of the corresponding element of the sample.

Generally, the structures and operations of ion-based and optical-based spectrometers and their many variants are known to persons skilled in the art, and accordingly have been only briefly described herein as necessary for understanding the subject matter being disclosed.

From the foregoing, it may be seen that one or more embodiments disclosed herein may provide one or more of the following advantages. One or more of the embodiments provide cost-effective means for ambient desorption/ionization, such as microwave energy, as compared to laser-based techniques such as MALDI. One or more of the embodiments enable the direct analysis of small molecules that cannot be analyzed by MALDI because the matrix compounds used in MALDI have molecular weights less than 300 and obscure small molecule analyte peaks in this range. Additionally, one or more of the embodiments enable careful control of sample desorption and ionization for better quantitation compared with other ambient plasma sampling techniques (e.g., DART). The independent control over thermal desorption and plasma ionization/excitation attainable by one or more embodiments disclosed herein makes it possible to a) ramp the temperature of the sample for simple separation of compounds based on volatility, b) perform heat-assisted derivatization or c) evaporate solvents, before excitation/ionization (which is not possible with techniques in which the desorption and ionization are convolved, e.g., MALDI, DART, DESI). In contrast, when using DART the plasma gas stream is heated to provide thermal desorption of the analyte molecules, which requires additional heating components and leads to sample heating that is less controlled and localized compared with the dielectric heating described herein. Additionally, the microwave plasma and other plasmas described herein may be formed in ambient air, or in any number of other gases (including nitrogen, argon, and helium). In contrast, typically the DART technique involves substantial flows of helium, which is costly. Additionally, embodiments disclosed herein are flexible enough to be applied to a range of spectrometric/spectroscopic techniques such as OES, MS, and IMS, unlike other techniques (e.g., DART, DESI, MALDI) that are employed only as front-end sampling/ionization for MS. Additionally, embodiments disclosed herein enable ambient sampling that requires no sample preparation, unlike traditional liquid chromatography MS (LC-MS), gas chromatography MS (GC-MS), inductively coupled plasma OED (ICP-OES), ICP-MS, microwave plasma atomic emission spectrometry (MP-AES), or MALDI techniques. Additionally, embodiments disclosed herein are capable of sampling directly from a substrate utilized for analytical separation such as TLC, gel electrophoresis, or the like.

Various embodiments have been described above primarily in the context of the generation and use of microwave excitation fields. However, one or more embodiments may be suitable for implementing direct current (DC) or alternating current (AC) excitation fields.

Referring to FIG. 1, as an example of embodiments that generate a DC plasma, the plasma generating component 132 may be an electrode of suitable geometry (e.g., plate, rod, needle, etc.), the power line 140 may be a wire, and the power connection 144 may be a contact pad, interconnect, solder bump, etc. The plasma generator 104 may include one or more additional electrodes (not shown) that are positioned, and electrically biased or grounded, as needed for generating the excitation field for striking the plasma at a desired location and spatial orientation. In some embodiments, the interface 116 or a portion thereof may be electrically conductive and serve as a biased or grounded counter-electrode for the plasma generating component 132. Alternatively or additionally, in embodiments entailing mass spectrometry (MS) or ion mobility spectrometry (IMS), the interface 116 or a portion thereof may be biased to assist in extracting analyte ions produced in the ionization region 128. In some embodiments, the plasma generating component 132 includes a curve, edge, or sharp feature (e.g., needle, pin, etc.) that facilitates producing a corona discharge plasma.

As an example of embodiments that generate an AC plasma, the plasma generating component 132 may be an electrode as just described. The AC power is fed to the plasma generating component 132 via the power line 140, and also to a second electrode to complete the circuit, e.g., the interface 116 or an additional electrode (not shown). In some embodiments, provided the sample support 108 is a dielectric material and is sufficiently thin, the second electrode may be located at the back surface 122, i.e., on the side of the sample support 108 opposite to the sample 112. In this case, the sample support 108 serves as a dielectric barrier between the plasma generating component 132 and the second electrode, and the plasma generated thereby may be of the type known as a dielectric barrier discharge (DBD) plasma.

EXEMPLARY EMBODIMENTS

Exemplary embodiments provided in accordance with the presently disclosed subject matter include, but are not limited to, the following:

1. An ion source, comprising: a plasma generator configured for supplying plasma at an ionization region proximate to a sample surface, the plasma generator comprising a plasma generating component configured for switching between operating in a desorption mode and in an ionization mode, wherein: in the desorption mode, the plasma generating component applies energy effective for heating the sample without generating plasma; and in the ionization mode, the plasma generating component applies energy effective for generating plasma from the plasma precursor gas; and an interface configured for transferring analyte ions or photons produced in the plasma to a spectrometer.

2. The ion source of embodiment 1, wherein the plasma generating component is movable relative to the sample surface, or the sample surface is movable relative to the plasma generating component, or both of the foregoing.

3. The ion source of embodiment 1 or 2, wherein the plasma generator comprises a chamber in which the plasma is generated, and the chamber comprises a plasma outlet positioned to direct the plasma to the ionization region.

4. The ion source of embodiment 3, wherein the plasma outlet is movable relative to the sample surface, or the sample surface is movable relative to the plasma outlet, or both of the foregoing.

5. The ion source of embodiment 1, wherein the plasma generating component is on a side of the sample support opposite to the sample surface, and the energy is coupled into the ionization region through a thickness of the sample support.

6. The ion source of any of the preceding embodiments, wherein the plasma generating component comprises a microstrip resonator.

7. The ion source of embodiment 1, wherein the plasma generating component comprises a waveguide, the waveguide comprising an electromagnetic field-focusing element and a matching network for directing the energy to the field-focusing element.

8. The ion source of embodiment 7, wherein the plasma generator is configured for conducting at least one of a gas, analyte ions, and photons through the waveguide.

9. The ion source of embodiment 7 or 8, wherein the plasma generator comprises a sleeve surrounding the waveguide such that a channel is between the sleeve and the waveguide, and the plasma generator is configured for conducting at least one of a gas, analyte ions, and photons through the channel.

10. The ion source of any of embodiments 7 to 9, wherein the waveguide comprises a center conductor and an outer conductor surrounding the center conductor, and the center conductor comprises an end comprising the field-focusing element.

11. The ion source of embodiment 10, wherein the center conductor is hollow.

12. The ion source of embodiment 11, wherein the plasma generator is configured for conducting at least one of a gas, analyte ions, and photons through the center conductor, through the waveguide, or through both the center conductor and the waveguide.

13. The ion source of any of embodiments 7 to 12, wherein the field-focusing element comprises an aperture at an end of the waveguide, and the aperture has a cross-sectional area less than a cross-sectional area of the waveguide.

14. The ion source of any of embodiments 7 to 13, wherein the waveguide comprises a discontinuity partitioning the waveguide into a first waveguide portion and a second waveguide portion, and the second waveguide portion has a cross-sectional area less than a cross-sectional area of the first waveguide portion.

15. The ion source of any of embodiments 1 to 14, wherein the plasma generating component is configured for applying microwave energy.

16. The ion source of any of embodiments 1 to 15, wherein the plasma generator is configured for switching between operating in the desorption mode and the ionization mode by switching between extinguishing the plasma and striking the plasma.

17. The ion source of embodiment 16, wherein the plasma generator is configured for switching between extinguishing the plasma and striking the plasma according to a configuration selected from the group consisting of: switching application of the energy between an OFF state and an ON state; switching application of the energy between a low power state and a high power state; switching application of the energy between a non-resonant drive frequency and a resonant drive frequency; switching a flow of the plasma precursor gas between an OFF state and an ON state; switching a flow of the plasma precursor gas between a low-flow state and a high-flow state; switching the plasma precursor gas between a first composition having a high threshold for plasma formation and a second composition having a low threshold for plasma formation; and a combination or two or more of the foregoing.

18. The ion source of any of embodiments 1 to 17, wherein the plasma generator is configured for switching between operating in the desorption mode and the ionization mode by moving the plasma generating component to change a distance between the plasma generating component and the sample surface.

19. The ion source of any of embodiments 1 to 18, comprising a sample support for supporting the sample.

20. The ion source of embodiment 19, wherein the sample support comprises a planar substrate configured for performing analytical separation on the sample surface.

21. The ion source of embodiment 19 or 20, wherein the sample support comprises a material responsive to dielectric heating.

22. The ion source of any of embodiments 19 to 21, comprising a dielectric heating material, wherein the sample support is disposed on the dielectric heating material.

23. The ion source of any of embodiments 19 to 22, comprising a stage or an end effector configured for moving the sample support along one or more directions.

24. An ion source, comprising: a planar sample support comprising a sample surface and configured for performing analytical separation on the sample surface; and a plasma generator configured for supplying plasma at an ionization region proximate to the sample surface, the plasma generator comprising a gas outlet for supplying a plasma precursor gas, and a plasma generating component configured for generating a localized microwave energy field.

25. The ion source of embodiment 24, wherein the plasma generator is configured for switching between operating in a desorption mode and in an ionization mode, and: in the desorption mode, the plasma generating component applies energy effective for heating the sample without generating plasma; and in the ionization mode, the plasma generating component applies energy effective for generating plasma from the plasma precursor gas.

26. The ion source of embodiment 24 or 25, wherein the planar sample support is configured for performing chromatographic-based or electrophoretic-based separation.

27. The ion source of any of embodiments 24 to 26, wherein the plasma generating component is movable relative to the sample surface, or the sample surface is movable relative to the plasma generating component, or both of the foregoing.

28. The ion source of any of embodiments 24 to 27, wherein the plasma generating component is on a side of the sample support opposite to the sample surface, and the energy is coupled into the ionization region through a thickness of the sample support.

29. A spectrometry system, comprising: an ion source according to any of the preceding embodiments; and an analyzer.

30. The spectrometry system of embodiment 29, wherein the analyzer comprises an ion analyzer, a mass analyzer, or an ion mobility drift cell.

31. The spectrometry system of embodiment 29, wherein the analyzer comprises an optical analyzer and the interface comprises a photon guide.

32. A method for ionizing a sample, the method comprising: providing a sample; desorbing analytes from the sample by applying energy under conditions effective for heating the sample without actively generating plasma; and generating plasma above a sample surface of the sample by applying the energy under conditions effective for generating the plasma, wherein the plasma ionizes the desorbed analytes.

33. The method of embodiment 32, comprising supporting the sample on a sample support.

34. The method of embodiment 33, comprising performing analytical separation on the sample support.

35. The method of embodiment 33, wherein providing the sample comprises providing a plurality of samples spatially separated on the sample support.

36. The method of embodiment 35, wherein providing the plurality of samples comprises dispensing the samples onto the sample support, or performing analytical separation on an initial sample on the sample support to produce a plurality of samples comprising separated analytes.

37. The method of embodiment 35 or 36, wherein applying the energy comprises generating a localized energy field, and further comprising: selecting one or more of the samples; moving the sample support to sequentially locate the one or more selected samples at the energy field; and at each iteration of the sequence, performing the steps of desorbing analytes and generating plasma.

38. The method of any of embodiments 32 to 37, comprising controlling a location at which the plasma is generated relative to a location at which the desorbed analytes interact with the plasma, so as to control whether the desorbed analytes predominantly interact with charged species, metastable species, or photons of the plasma.

39. The method of any of embodiments 32 to 38, comprising supplying the plasma at an ionization region above the sample surface by generating the plasma at the ionization region, or by generating the plasma at a distance from the ionization region and flowing the plasma to the ionization region.

40. The method of any of embodiments 32 to 37, wherein applying the energy comprises coupling the energy through a sample support below the sample surface to a region above the sample surface.

41. The method of any of embodiments 32 to 40, comprising desorbing analytes from a subsurface region of the sample.

42. The method of embodiment 41, wherein applying energy comprises operating a plasma generating component, and desorbing analytes from the subsurface region comprises at least one of: moving a field-focusing element of the plasma generating component close enough to the sample surface to effect desorption from the subsurface region; moving a field-focusing element of the plasma generating component into contact with the sample surface; moving a field-focusing element of the plasma generating component such that the field-focusing element penetrates the sample surface.

43. The method of embodiment 32, wherein applying the energy comprises operating a plasma generating component comprising a waveguide configured for directing the energy toward the sample surface, and further comprising conducting at least one of a gas, analyte ions, and photons through the cavity.

44. The method of any of embodiments 32 to 43, wherein applying the energy comprises applying microwave energy.

45. The method of any of embodiments 32 to 44, comprising switching between desorbing analytes and ionizing analytes.

46. The method of embodiment 45, wherein switching is selected from the group consisting of: switching application of the energy between an OFF state and an ON state; switching application of the energy between a low power state and a high power state; switching application of the energy between a non-resonant drive frequency and a resonant drive frequency; switching a flow of the plasma precursor gas between an OFF state and an ON state; switching a flow of the plasma precursor gas between a low-flow state and a high-flow state; switching the plasma precursor gas between a first composition having a high threshold for plasma formation and a second composition having a low threshold for plasma formation; moving a plasma generating component to change a distance between the plasma generating component and the sample surface; and a combination or two or more of the foregoing.

47. The method of any of embodiments 32 to 46, wherein desorbing analytes comprises heating the sample.

48. The method of embodiment 47, wherein heating the sample comprises heating the sample directly by dielectric heating of one or more components of the sample, or heating a bulk material adjacent to the sample surface by dielectric heating of the bulk material.

49. A method for ionizing a sample, the method comprising: performing analytical separation on an initial sample on a sample surface of a planar sample support to produce a plurality of samples on the sample surface; and applying a localized microwave energy field to generate plasma above the sample surface proximate to a selected one of the samples, wherein the plasma ionizes analytes of the selected sample.

50. The method of any of the preceding embodiments, comprising transmitting analyte ions or photons produced in the plasma to a spectrometer.

51. A method for analyzing a sample, the method comprising: ionizing a sample according to any of the preceding embodiments to form analyte ions or photons; and measuring an attribute of the analyte ions or photons.

52. The method of embodiment 51, wherein measuring the attribute comprises measuring ion mass, ion drift time, or photon wavelength.

53. A spectrometry system configured for performing the method of any of the preceding embodiments.

It will be understood that terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. An ion source, comprising:
   a plasma generator configured for supplying plasma at an ionization region proximate to a sample surface, the plasma generator comprising a plasma generating component, wherein the plasma generator is configured for switching between operating in a desorption mode and in an ionization mode, wherein:
      in the desorption mode, the plasma generating component applies energy effective for heating a sample disposed at or part of the sample surface without exposing the sample to active plasma, wherein the energy is applied to a component selected from the group consisting of the sample, the sample surface, a sample support on which the sample is supported, a plasma precursor gas, and a combination of two or more of the foregoing; and
      in the ionization mode, the plasma generating component applies energy to the plasma precursor gas effective for generating active plasma from the plasma precursor gas and exposing the sample to the active plasma; and
   an interface configured for transferring analyte ions or photons produced in the plasma generated by the plasma generating component to a spectrometer.

2. The ion source of claim 1, wherein the plasma generating component is movable relative to the sample surface, or the sample surface is movable relative to the plasma generating component, or both of the foregoing.

3. The ion source of claim 1, wherein the plasma generator comprises a chamber in which the plasma is generated, and the chamber comprises a plasma outlet positioned to direct the plasma to the ionization region.

4. The ion source of claim 1, wherein the plasma generating component is on a side of the sample support opposite to the sample surface, and the energy is coupled into the ionization region through a thickness of the sample support.

5. The ion source of claim 1, wherein the plasma generating component comprises a microstrip resonator.

6. The ion source of claim 1, wherein the plasma generating component comprises a waveguide, the waveguide comprising an electromagnetic field-focusing element and a matching network for directing the energy to the field-focusing element.

7. The ion source of claim 6, comprising a configuration selected from the group consisting of:
   the plasma generator is configured for conducting at least one of a gas, analyte ions, and photons through the waveguide;
   the plasma generator comprises a sleeve surrounding the waveguide such that a channel is between the sleeve and the waveguide, and the plasma generator is configured for conducting at least one of a gas, analyte ions, and photons through the channel; and
   both of the foregoing.

8. The ion source of claim 6, wherein the waveguide comprises a center conductor and an outer conductor surrounding the center conductor, and the center conductor comprises an end comprising the field-focusing element.

9. The ion source of claim 8, wherein the center conductor is hollow, and the plasma generator is configured for conducting at least one of a gas, analyte ions, and photons through the center conductor, through the waveguide, or through both the center conductor and the waveguide.

10. The ion source of claim 6, wherein the field-focusing element comprises an aperture at an end of the waveguide, and the aperture has a cross-sectional area less than a cross-sectional area of the waveguide.

11. The ion source of claim 1, wherein the plasma generating component is configured for applying microwave energy.

12. The ion source of claim 1, wherein the plasma generator is configured for switching between operating in the desorption mode and the ionization mode according to a configuration selected from the group consisting of:
   switching application of the energy between an OFF state and an ON state;
   switching application of the energy between a low power state and a high power state;
   switching application of the energy between a non-resonant drive frequency and a resonant drive frequency;
   switching a flow of the plasma precursor gas between an OFF state and an ON state;
   switching a flow of the plasma precursor gas between a low-flow state and a high-flow state;
   switching the plasma precursor gas between a first composition having a high threshold for plasma formation and a second composition having a low threshold for plasma formation;
   moving the plasma generating component to change a distance between the plasma generating component and the sample surface; and
   a combination or two or more of the foregoing.

13. The ion source of claim 1, comprising a sample support, the sample support comprising a configuration selected from the group consisting of:
   the sample support comprises a planar substrate;
   the sample support is configured for performing analytical separation on the sample surface;
   the sample support comprises a material responsive to dielectric heating;
   the sample support is disposed on a dielectric heating material;
   the sample support is in contact with a stage or an end effector configured for moving the sample support along one or more directions; and
   a combination of two or more of the foregoing.

14. An ion source, comprising:
   a planar sample support comprising a sample surface and configured for performing analytical separation on the sample surface; and
   a plasma generator configured for supplying plasma at an ionization region proximate to the sample surface, the plasma generator comprising a gas outlet for supplying a plasma precursor gas, and a plasma generating component configured for generating a localized microwave energy field, and the plasma generator configured for switching between operating in a desorption mode and in an ionization mode, wherein:
      in the desorption mode, the plasma generating component applies energy effective for heating a sample disposed at or part of the sample surface without exposing the sample to active plasma, wherein the energy is applied to a component selected from the group consisting of the sample, the sample surface, a sample support on which the sample is supported, a plasma precursor gas, and a combination of two or more of the foregoing; and in the ionization mode, the plasma generating component applies energy to the plasma precursor gas effective for generating active plasma from the plasma precursor gas and exposing the sample to the active plasma.

15. A method for ionizing a sample, the method comprising:

providing a sample;

desorbing analytes from the sample by operating a plasma generating component to apply energy under conditions effective for heating the sample without actively generating plasma, wherein the energy is applied to a component selected from the group consisting of the sample, a sample surface of the sample, a sample support on which the sample is supported, a plasma precursor gas, and a combination of two or more of the foregoing; and generating plasma above a sample surface of the sample by operating a plasma generating component to apply energy to the plasma precursor gas under conditions effective for generating the plasma, wherein the plasma ionizes the desorbed analytes.

16. The method of claim 15, comprising supporting or adsorbing the sample on a sample support.

17. The method of claim 16, wherein providing the sample comprises providing a plurality of samples spatially separated on the sample support.

18. The method of claim 17, wherein providing the plurality of samples comprises dispensing the samples onto the sample support, or performing analytical separation on an initial sample on the sample support to produce a plurality of samples comprising separated analytes.

19. The method of claim 17, wherein applying the energy comprises generating a localized energy field, and further comprising:

selecting one or more of the samples;

moving the sample support to sequentially locate the one or more selected samples at the energy field; and at each iteration of the sequence, performing the steps of desorbing analytes and generating plasma.

20. The method of claim 15, comprising desorbing analytes from a subsurface region of the sample.

* * * * *

UNITED STATES PATENT AND TRADEMARK OFFICE
CERTIFICATE OF CORRECTION

PATENT NO. : 9,875,884 B2
APPLICATION NO. : 14/634745
DATED : January 23, 2018
INVENTOR(S) : Viorica Lopez-Avila et al.

It is certified that error appears in the above-identified patent and that said Letters Patent is hereby corrected as shown below:

On the Title Page

On the page 2, in Column 2, under "Other Publications", Line 65, delete "chromatogapghy" and insert -- chromatography --, therefor.

In the Specification

In Column 24, Lines 25-26, delete "a combination or two or more" and insert -- a combination of two or more --, therefor.

In Column 26, Lines 33-34, delete "a combination or two or more" and insert -- a combination of two or more --, therefor.

In the Claims

In Column 28, Lines 38, in Claim 12, delete "a combination or two or more" and insert -- a combination of two or more --, therefor.

Signed and Sealed this
Twenty-ninth Day of May, 2018

Andrei Iancu
*Director of the United States Patent and Trademark Office*